US006440674B1

(12) United States Patent
Misra et al.

(10) Patent No.: US 6,440,674 B1
(45) Date of Patent: Aug. 27, 2002

(54) PLANT PROMOTER DERIVED FROM LUMINAL BINDING PROTEIN GENE AND METHODS FOR ITS USE

(75) Inventors: Santosh Misra; Benjamin S. Forward, both of Victoria (CA)

(73) Assignee: University of Victoria Innovation and Development Corporation, Victoria (CA)

( * ) Notice: Subject to any disclaimer, the term of this patent is extended or adjusted under 35 U.S.C. 154(b) by 0 days.

(21) Appl. No.: 09/632,538

(22) Filed: Aug. 4, 2000

(51) Int. Cl.⁷ .................................................. C12Q 1/68
(52) U.S. Cl. ..................... 435/6; 435/320.1; 435/91; 435/172.1; 435/172.3; 935/6; 935/25; 935/30; 935/33; 935/41; 536/24.1; 536/27
(58) Field of Search ................... 536/24.1, 27; 435/6, 435/320.1, 91, 172.1, 172.3; 935/6, 25, 30, 33, 41

(56) References Cited

U.S. PATENT DOCUMENTS

| | | |
|---|---|---|
| 5,023,179 A | 6/1991 | Lam et al. |
| 5,097,025 A | 3/1992 | Benfey et al. |
| 5,290,924 A | 3/1994 | Last et al. |
| 5,412,085 A | 5/1995 | Allen et al. |
| 5,689,053 A | 11/1997 | Robert et al. |
| 5,907,086 A | 5/1999 | Neill et al. |

FOREIGN PATENT DOCUMENTS

WO      WO 99/14316     3/1999

OTHER PUBLICATIONS

Genbank Accession No.: CAA89834, Misra.
Genbank Accession No.: T09500, Tranberger and Misra.
Gething, Mary–Jane, "Role and Regulation of the ER Chaperone BiP," *Cell & Dev. Biol.* 10:465–472 (1999).
Wrobel et al., "Comparative Analysis of BiP Gene Expression in Maize Endosperm," *Gene* 204:105–113 (1997).
Li et al., "Molecular Chaperone Calnexin Associates with the Vacuolar $H^+$–ATPase from Oat Seedlings," *Plant Cell* 10:119–130 (1998).
Muench et al., "Molecular Cloning, Expression and Subcellular Localization of a BiP Homolog from Rice Endosperm Tissue," *Plant Cell Physiol.* 38(4):404–412 (1997).
Leborgne–Castel et al., "Overexpression of BiP in Tobacco Alleviates Endoplasmic Reticulum Stress," *Plant Cell* 11:459–469 (1999).

*Primary Examiner*—W. Gary Jones
*Assistant Examiner*—Janell E. Taylor
(74) *Attorney, Agent, or Firm*—Klarquist Sparkman, LLP

(57) ABSTRACT

The invention provides a luminal binding protein promoter (PmBiPPro1), deletions thereof, and variants thereof. The promoter is useful for, among other things, directing the expression of transgenes.

31 Claims, 18 Drawing Sheets

1) List of Putative cis-elements in PmBiPProl

| Site Name | Loc.(Str.) | Sequence | Description |
|---|---|---|---|
| -300ELEMENT | 1153 (+) | TGHAAARK | Element is present in the promoter of the barley B-hordein gene and the alpha-gliadin, gamma-gliadin, and low molecular weight glutenin genes of wheat [39]. |
| 2SSEEDPROTBANAP | 2044 (+) | CAAACAC | Conserved in many storage-protein gene promoters and may be important for high activity of the napA promoter [37]. |
| | | | ARF (auxin response factor) binding site found in the promoters of primary/early auxin response genes of Arabidopsis thaliana. Many different ARFs are known and can act as activators and repressors [42, 43]. |
| ASF1MOTIFCAMV | 2145 (+) | TGACG | TGACG motifs are found in many promoters and are involved in transcriptional activation of several genes by auxin and/or salicylic acid [25, 38]. |
| ASF1MOTIFCAMV | 2050 (-) | TGACG | |
| | | | Light-induced transcriptional repression of the pea asparagine synthase (AS1) gene [33]. |
| | | | Box II found in the tobacco plastid atpB gene promoter and is conserved in several NCII (nonconsensus type II) promoters of plastid genes [22]. |
| BOXIIPCCHS | 2069 (+) | ACGTGGC | Core of "Box II/G box" found in the parsley chalcone synthase (chs) genes and is essential for light regulation [38]. |
| | | | "CAAT promoter consensus sequence" found in the pea legumin (legA) gene [35]. |
| CAATBOX1 | 1155 (+) | CAAT | |
| CAATBOX1 | 1320 (+) | CAAT | |
| CAATBOX1 | 1362 (+) | CAAT | |
| CAATBOX1 | 1371 (+) | CAAT | |
| CAATBOX1 | 1578 (+) | CAAT | |
| CAATBOX1 | 1815 (+) | CAAT | |
| CAATBOX1 | 1805 (+) | CAAT | |
| CAATBOX1 | 1831 (+) | CAAT | |
| CAATBOX1 | 1965 (+) | CAAT | |
| CAATBOX1 | 2028 (+) | CAAT | |
| CAATBOX1 | 2053 (+) | CAAT | |

Figure 5A

| Element | Position | Sequence | Description |
|---|---|---|---|
| CAATBOX1 | ... (-) | CAAT | |
| CAATBOX1 | ... (-) | CAAT | |
| CAATBOX1 | ... (-) | CAAT | |
| CAATBOX1 | ... (-) | CAAT | |
| CAATBOX1 | 2037 (-) | CAAT | |
| CAATBOX1 | 2212 (-) | CAAT | |
| CAATBOX1 | 2236 (-) | CAAT | |
| CACGTGMOTIF | ... (+) | CACGTG | Represents the core of "G-box" [15] and is found in the promoter region of light-responsive genes such as rbcS and chalcone synthase (chs). It is also commonly found in other unrelated genes [47]. |
| CACGTGMOTIF | ... (+) | CACGTG | |
| CACGTGMOTIF | 2021 (+) | CACGTG | |
| CACGTGMOTIF | 2119 (+) | CACGTG | |
| CACGTGMOTIF | ... (-) | CACGTG | |
| CACGTGMOTIF | ... (-) | CACGTG | |
| CACGTGMOTIF | 2031 (-) | CACGTG | |
| CACGTGMOTIF | 2119 (-) | CACGTG | |
| CANBNNAPA | ... (+) | CNAACAC | Comprises the core of the "(CA)n element" in storage protein genes in Brasica napus. Confers embryo and endosperm-specific transcription of napin storage protein gene (napA). Can possibly function in activation and repression to confer seed specificity. [11]. |
| CANBNNAPA | ... (+) | CNAACAC | |
| CANBNNAPA | 2044 (+) | CNAACAC | |
| CANBNNAPA | 2122 (-) | CNAACAC | |
| CEREALGLUTBOXP | ... (-) | TGAAAACT | Referred to as the "cereal glutenin box" and is found in the pea legumin gene (legA). The sequence is homologous to the cereal glutenin gene control element ("-300 element" see above) [35]. |
| DOFCOREZM | ... (+) | AAAG | Core site is required for binding of Dof DNA binding proteins in maize. Surrounding nucleotides can influence binding. Dof proteins found only in plants and contain only a single zinc finger. Four Dof proteins, Dof1, Dof2, Dof3 and PBF, have been isolated from maize and PBF is an endosperm specific Dof protein that binds to the prolamin box [48]. |
| DOFCOREZM | ... (+) | AAAG | |
| DOFCOREZM | ... (+) | AAAG | |
| DOFCOREZM | ... (+) | AAAG | |
| DOFCOREZM | ... (+) | AAAG | |
| DOFCOREZM | ... (+) | AAAG | |
| DOFCOREZM | ... (+) | AAAG | |
| DOFCOREZM | 2129 (+) | AAAG | |
| DOFCOREZM | 2167 (+) | AAAG | |

Figure 5B

| | | |
|---|---|---|
| DOFCOREZM | 1122 (+) AAAG | |
| DOFCOREZM | 1571 (+) AAAG | |
| DOFCOREZM | 1980 (+) AAAG | |
| DPBFCOREDCDC3 | 1043 (+) ACACNNG | Consensus binding core sequence for a novel class of bZIP transcription factors, DPBF-1 and 2 (Dc3 promoter-binding factor-1 and 2). Elements are found in the carrot Dc3 gene (a LEA gene) which is expressed in an embryo-specific and ABA inducible manner [23]. |
| DPBFCOREDCDC3 | 1347 (+) ACACNNG | |
| DPBFCOREDCDC3 | 1785 (+) ACACNNG | |
| DPBFCOREDCDC3 | 1790 (+) ACACNNG | |
| DPBFCOREDCDC3 | 2020 (+) ACACNNG | |
| DPBFCOREDCDC3 | 2118 (+) ACACNNG | |
| DPBFCOREDCDC3 | 1256 (-) ACACNNG | |
| DPBFCOREDCDC3 | 1791 (-) ACACNNG | |
| DPBFCOREDCDC3 | 2021 (-) ACACNNG | |
| DPBFCOREDCDC3 | 2119 (-) ACACNNG | |
| EBOXBNNAPA | | Comprises the E-box of storage-protein gene napA of Brassica napus [37]. |
| EBOXBNNAPA | 1383 (+) CANNTG | |
| EBOXBNNAPA | 1483 (+) CANNTG | |
| EBOXBNNAPA | 1755 (+) CANNTG | |
| EBOXBNNAPA | 1791 (+) CANNTG | |
| EBOXBNNAPA | 1795 (+) CANNTG | |
| EBOXBNNAPA | 1805 (+) CANNTG | |
| EBOXBNNAPA | 2021 (+) CANNTG | |
| EBOXBNNAPA | 2119 (+) CANNTG | |
| EBOXBNNAPA | 1383 (-) CANNTG | |
| EBOXBNNAPA | 1483 (-) CANNTG | |
| EBOXBNNAPA | 1755 (-) CANNTG | |
| EBOXBNNAPA | 1791 (-) CANNTG | |
| EBOXBNNAPA | 1795 (-) CANNTG | |
| EBOXBNNAPA | 1805 (-) CANNTG | |
| EBOXBNNAPA | 2021 (-) CANNTG | |
| EBOXBNNAPA | 2119 (-) CANNTG | |
| GATAMOTIFCAMV | | GATA motif found in the Cauliflower Mosaic Virus 35S promoter and binds the transcription factor ASF-2 [18, 26] |
| GATAMOTIFCAMV | 1118 (+) GATA | |
| GATAMOTIFCAMV | 1250 (+) GATA | |
| GATAMOTIFCAMV | 1251 (+) GATA | |
| | (+) GATA | |
| | (+) GATA | |
| | (+) GATA | |
| GATAMOTIFCAMV | 1204 (+) GATA | |

Figure 5C

| | | | |
|---|---|---|---|
| | | | Consensus GT-1 transcription factor binding site found in many light-regulated genes [39, 45]. |
| | | | |
| | | | Critical element for binding of GT-1 transcription factor to box II of rbcS gene [19, 38, 45]. |
| HEXMOTIFTAH3H4 | 2049 | (+) ACGTCA | Element found in the promoter of wheat histone genes H3 and H4 and binds the HBP-1A and HBP-1B transcription factors [30, 31]. |
| | | | Conserved motif located in the promoter region of light-regulated genes such as tomato and Arabidopsis rbcS (Donald, 1990 #284; Giuliano, 1988 #285]. |
| | | | Conserved sequence located in the promoter region of light-regulated genes of both monocots and dicots [38]. Also see IBOX above. |
| | | | A low-temperature-responsive element located in the barley blt4.9 (a non-specific lipid transfer protein) gene promoter [10]. |
| | | | Core of the low temperature responsive element (LTRE) of cor15a gene from Arabidopsis and involved in the cold induction of the BN115 gene of Brassica napus [3, 46]. |
| | | | Involved in the attachment of genes to the nuclear matrix [17]. |

Figure 5D

| Site | Position | Description |
|---|---|---|
| MNF1ZMPPC1 | 2219 (-) GTGCCCTT | Recognition site of the MNF1 DNA binding protein is located in the maize phosphoenolpyruvate carboxylase (Ppc1) gene promoter and is involved in light induction [32]. |
| MYB26PS | 1950 (+) CTTAAGTT | Binding site for Myb26 at the c-Myb and P-box-like binding sites located in the promoter regions of several phenylpropanoid biosynthetic genes. This site is identical to P-box in maize, and to Myb305 binding site in snapdragon [41]. |
| | | The binding site for ATMYB2, an Arabidopsis MYB homolog involved in regulation of genes that are responsive to water stress [44]. |
| | | Binding site for MYB (ATMYB2) in dehydration-responsive gene rd22 of Arabidopsis and is involved in induction by ABA [1, 7]. |
| MYBCORE | 1774 (+) CNGTTR | Binding site for at least two plant MYB proteins, ATMYB1 and ATMYB2, from Arabidopsis (See Above). Also involved in the regulation of flavonoid biosynthesis in petunia by another MYB protein (MYB.Ph3) [36, 44]. |
| MYBPLANT | 1351 (+) MACCWAMC | Consensus plant MYB binding site related to box P in promoters of phenylpropanoid biosynthetic genes such as PAL and CHS [34]. M=A/C; W=A/T. |
| MYBPLANT | 1650 (-) MACCWAMC | |
| MYBPZM | 1357 (+) CCWACC | Core of consensus maize P myb homolog binding site. Maize P gene specifies red pigmentation of the kernel pericarp, cob, and other floral organs by activating a subset of phenylpropanoid biosynthetic genes [20]. W=A/T |
| MYBPZM | 1872 (-) CCWACC | |
| | | Core motif of a potato MYB homolog, MybSt1, binding site involved in transcriptional activation [4]. |
| MYBST1 | 1347 (-) GGATA | |
| MYBST1 | 1383 (-) GGATA | |
| | | A negative regulatory region in the promoter region of the Brassica napus extensin gene, extA. Removal of this element lead to expression in all tissues within the stem internode, petiole and root [12]. |
| | | NtBBF1 (Tobacco Dof protein homologue) binding site in the Agrobacterium rhizogenes rolB gene and is required for tissue-specific expression and auxin induction [6]. |

Figure 5E

| Element | Position | Sequence | Description |
|---|---|---|---|
| POLLEN1LELAT52 | 1336 (+) | AGAAA | One of two co-dependent regulatory elements responsible for pollen specific activation of the lat52 gene (a cysteine-rich protein) in tomato. Another element, POLLEN2LELAT52 (TCCACCATA) is required for pollen specific expression [5]. |
| POLLEN1LELAT52 | 1599 (+) | AGAAA | |
| POLLEN1LELAT52 | 1941 (+) | AGAAA | |
| POLLEN1LELAT52 | 1735 (-) | AGAAA | |
| POLLEN1LELAT52 | 2190 (-) | AGAAA | |
| PYRIMIDINEBOXHV | 1456 (+) | TTTTTCC | The Pyrimidine box found in the barley cysteine proteinase gene, EPB-1, promoter and is required for GA induction [8]. |
| QARBNEXTA | 1061 (-) | AACGTGT | Quantitative activator region (QAR) in the promoter of the Brassica napus extensin gene, extA [12]. |
| QELEMENTZMZM13 | 1928 (+) | AGGTCA | A quantitative-element in the pollen-specific maize ZM13 gene promoter involved in expression enhancing activity [21]. |
| RBCSCONSENSUS | 1539 (+) | AATCCAA | Ribulose-1,5-bisphosphate carboxylase (rbcS) general promoter consensus sequence [9, 29]. |
| ROOTMOTIFTAPOX1 | 1914 (+) | ATATT | Motif found in the promoters of rolD and the root-specific wheat peroxidase (POX1) [13]. |
| ROOTMOTIFTAPOX1 | 1706 (-) | ATATT | |
| ROOTMOTIFTAPOX1 | 1913 (-) | ATATT | |
| ROOTMOTIFTAPOX1 | 2898 (-) | ATATT | |
| RYREPEATBNNAPA | | | "RY repeat" required for the seed specific expression of the Brassica napus napA gene. This element is part of an RY/G box complex containing two RY repeats and a G-box) [14]. |
| RYREPEATGMGY2 | | | Found in the promoter region of the soybean glycinin gene (Gy2) [27]. |
| RYREPEATLEGUMINBOX | | | Another "RY repeat" found in seed-storage protein genes in legumes such as soybean [16]. |
| SIFBOXSORPS1L21 | 1680 (+) | ATGGTA | "S1F box" conserved in the spinach RPS1 and RPL21 genes that encode the plastid ribosomal proteins S1 and L21, respectively. Possibly a negative regulator decreasing the promoter activity of both genes [24, 49]. |
| SEF3MOTIFGM | 1355 (+) | AACCCA | Motif found in the promoter region of beta-conglycinin (7S globulin) gene of soybean [2, 28]. Element binds SEF3 (soybean embryo factor 3). |

Figure 5F

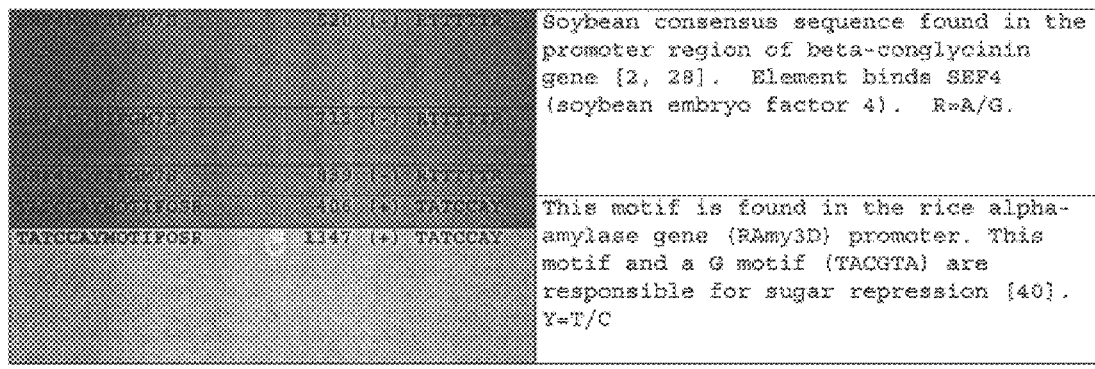

Figure 5G

Literature Cited

1. Abe H, Yamaguchi-Shinozaki K, Urao T, Iwasaki T, Hosokawa D, Shinozaki K: Role of arabidopsis MYC and MYB homologs in drought- and abscisic acid- regulated gene expression. Plant Cell 9: 1859-68 (1997).
2. Allen RD, Bernier F, Lessard PA, Beachy RN: Nuclear factors interact with a soybean beta-conglycinin enhancer. Plant Cell 1: 623-31 (1989).
3. Baker SS, Wilhelm KS, Thomashow MF: The 5'-region of Arabidopsis thaliana cor15a has cis-acting elements that confer cold-, drought- and ABA-regulated gene expression. Plant Mol Biol 24: 701-13 (1994).
4. Baranowskij N, Frohberg C, Prat S, Willmitzer L: A novel DNA binding protein with homology to Myb oncoproteins containing only one repeat can function as a transcriptional activator. Embo J 13: 5383-92 (1994).
5. Bate N, Twell D: Functional architecture of a late pollen promoter: pollen-specific transcription is developmentally regulated by multiple stage-specific and co-dependent activator elements. Plant Mol Biol 37: 859-69 (1998).
6. Baumann K, De Paolis A, Costantino P, Gualberti G: The DNA binding site of the Dof protein NtBBF1 is essential for tissue- specific and auxin-regulated expression of the rolB oncogene in plants. Plant Cell 11: 323-34 (1999).
7. Busk PK, Pages M: Regulation of abscisic acid-induced transcription. Plant Mol Biol 37: 425-35 (1998).
8. Cercos M, Gomez-Cadenas A, Ho TH: Hormonal regulation of a cysteine proteinase gene, EPB-1, in barley aleurone layers: cis- and trans-acting elements involved in the co- ordinated gene expression regulated by gibberellins and abscisic acid. Plant J 19: 107-118 (1999).
9. Donald RG, Cashmore AR: Mutation of either G box or I box sequences profoundly affects expression from the Arabidopsis rbcS-1A promoter. Embo J 9: 1717-26 (1990).
10. Dunn MA, White AJ, Vural S, Hughes MA: Identification of promoter elements in a low-temperature-responsive gene (blt4.9) from barley (Hordeum vulgare L.). Plant Mol Biol 38: 551-64 (1998).
11. Ellerstrom M, Stalberg K, Ezcurra I, Rask L: Functional dissection of a napin gene promoter: identification of promoter elements required for embryo and endosperm-specific transcription. Plant Mol Biol 32: 1019-27 (1996).
12. Elliott KA, Shirsat AH: Promoter regions of the extA extensin gene from Brassica napus control activation in response to wounding and tensile stress (published erratum appears in Plant Mol Biol 1998 Nov;38(5):913). Plant Mol Biol 37: 675-87 (1998).
13. Elmayan T, Tepfer M: Evaluation in tobacco of the organ specificity and strength of the rolD promoter, domain A of the 35S promoter and the 35S2 promoter. Transgenic Res 4: 388-96 (1995).

14. Ezcurra I, Ellerstrom M, Wycliffe P, Stalberg K, Rask L: Interaction between composite elements in the napA promoter: both the B- box ABA-responsive complex and the RY/G complex are necessary for seed- specific expression. Plant Mol Biol 40: 699-709 (1999).

15. Foster R, Izawa T, Chua NH: Plant bZIP proteins gather at ACGT elements. Faseb J 8: 192-200 (1994).

16. Fujiwara T, Beachy RN: Tissue-specific and temporal regulation of a beta-conglycinin gene: roles of the RY repeat and other cis-acting elements. Plant Mol Biol 24: 261-72 (1994).

17. Gasser SM, Amati BB, Cardenas ME, Hofmann JF: Studies on scaffold attachment sites and their relation to genome function. Int Rev Cytol 119: 57-96 (1989).

18. Gilmartin PM, Sarokin L, Memelink J, Chua NH: Molecular light switches for plant genes. Plant Cell 2: 369-78 (1990).

19. Green PJ, Yong MH, Cuozzo M, Kano-Murakami Y, Silverstein P, Chua NH: Binding site requirements for pea nuclear protein factor GT-1 correlate with sequences required for light-dependent transcriptional activation of the rbcS-3A gene. Embo J 7: 4035-44 (1988).

20. Grotewold E, Drummond BJ, Bowen B, Peterson T: The myb-homologous P gene controls phlobaphene pigmentation in maize floral organs by directly activating a flavonoid biosynthetic gene subset. Cell 76: 543-53 (1994).

21. Hamilton DA, Schwarz YH, Mascarenhas JP: A monocot pollen-specific promoter contains separable pollen-specific and quantitative elements. Plant Mol Biol 38: 663-9 (1998).

22. Kapoor S, Sugiura M: Identification of two essential sequence elements in the nonconsensus type II PatpB-290 plastid promoter by using plastid transcription extracts from cultured tobacco BY-2 cells [see comments]. Plant Cell 11: 1799-810 (1999).

23. Kim SY, Chung HJ, Thomas TL: Isolation of a novel class of bZIP transcription factors that interact with ABA-responsive and embryo-specification elements in the Dc3 promoter using a modified yeast one-hybrid system. Plant J 11: 1237-51 (1997).

24. Lagrange T, Franzetti B, Axelos M, Mache R, Lerbs-Mache S: Structure and expression of the nuclear gene coding for the chloroplast ribosomal protein L21: developmental regulation of a housekeeping gene by alternative promoters. Mol Cell Biol 13: 2614-22 (1993).

25. Lam E, Benfey PN, Gilmartin PM, Fang RX, Chua NH: Site-specific mutations alter in vitro factor binding and change promoter expression pattern in transgenic plants. Proc Natl Acad Sci U S A 86: 7890-4 (1989).

26. Lam E, Chua NH: ASF-2: a factor that binds to the cauliflower mosaic virus 35S promoter and a conserved GATA motif in Cab promoters. Plant Cell 1: 1147-56 (1989).

27. Lelievre J, Oliveira L, Nielsen N: 5'-CATGCAT-3' elements modulate the expression of glycinin genes. Plant Physiol 98: 387-391 (1992).

28. Lessard PA, Allen RD, Bernier F, Crispino JD, Fujiwara T, Beachy RN: Multiple nuclear factors interact with upstream sequences of differentially regulated beta-conglycinin genes. Plant Mol Biol 16: 397-413 (1991).

29. Manzara T, Gruissem W: Organization and expression of the genes encoding ribulose-1,5-bisphosphate carboxylase in higher plants. Photosynth Res 16: 117-139 (1988).

30. Mikami K, Nakayama T, Kawata T, Tabata T, Iwabuchi M: Specific interaction of nuclear protein HBP-1 with the conserved hexameric sequence ACGTCA in the regulatory region of wheat histone genes. Plant Cell Physiol 30: 107-119 (1989).

31. Mikami K, Tabata T, Kawata T, Nakayama T, Iwabuchi M: Nuclear protein(s) binding to the conserved DNA hexameric sequence postulated to

Figure 5H regulate transcription of wheat histone genes. FEBS Lett 223: 273-8 (1987).

32. Morishima A: Identification of preferred binding sites of a light-inducible DNA- binding factor (MNF1) within 5'-upstream sequence of C4-type phosphoenolpyruvate carboxylase gene in maize. Plant Mol Biol 38: 633-46 (1998).

33. Ngai N, Tsai FY, Coruzzi G: Light-induced transcriptional repression of the pea AS1 gene: identification of cis-elements and transfactors. Plant J 12: 1021-34 (1997).

34. Sablowski RW, Moyano E, Culianez-Macia FA, Schuch W, Martin C, Bevan M: A flower-specific Myb protein activates transcription of phenylpropanoid biosynthetic genes. Embo J 13: 128-37 (1994).

35. Shirsat A, Wilford N, Croy R, Boulter D: Sequences responsible for the tissue specific promoter activity of a pea legumin gene in tobacco. Mol Gen Genet 215: 326-31 (1989).

36. Solano R, Nieto C, Avila J, Canas L, Diaz I, Paz-Ares J: Dual DNA binding specificity of a petal epidermis-specific MYB transcription factor (MYB.Ph3) from Petunia hybrida. Embo J 14: 1773-84 (1995).

37. Stalberg K, Ellerstom M, Ezcurra I, Ablov S, Rask L: Disruption of an overlapping E-box/ABRE motif abolished high transcription of the napA storage-protein promoter in transgenic Brassica napus seeds. Planta 199: 515-9 (1996).

38. Terzaghi W, Cashmore A: Light-regulated transcription. Annu Rev Plant Physiol Plant Mol Biol 46: 445-474 (1995).

39. Thomas MS, Flavell RB: Identification of an enhancer element for the endosperm-specific expression of high molecular weight glutenin. Plant Cell 2: 1171-80 (1990).

40. Toyofuku K, Umemura T, Yamaguchi J: Promoter elements required for sugar-repression of the RAmy3D gene for alpha-amylase in rice. FEBS Lett 428: 275-80 (1998).

41. Uimari A, Strommer J: Myb26: a MYB-like protein of pea flowers with affinity for promoters of phenylpropanoid genes. Plant J 12: 1273-84 (1997).

42. Ulmasov T, Hagen G, Guilfoyle TJ: Activation and repression of transcription by auxin-response factors. Proc Natl Acad Sci U S A 96: 5844-9 (1999).

43. Ulmasov T, Hagen G, Guilfoyle TJ: Dimerization and DNA binding of auxin response factors. Plant J 19: 309-19 (1999).

44. Urao T, Yamaguchi-Shinozaki K, Urao S, Shinozaki K: An Arabidopsis myb homolog is induced by dehydration stress and its gene product binds to the conserved MYB recognition sequence. Plant Cell 5: 1529-39 (1993).

45. Villain P, Mache R, Zhou DX: The mechanism of GT element-mediated cell type-specific transcriptional control. J Biol Chem 271: 32593-8 (1996).

46. White TC, Simmonds D, Donaldson P, Singh J: Regulation of BN115, a low-temperature-responsive gene from winter Brassica napus. Plant Physiol 106: 917-28 (1994).

47. Williams ME, Foster R, Chua NH: Sequences flanking the hexameric G-box core CACGTG affect the specificity of protein binding. Plant Cell 4: 485-96 (1992).

48. Yanagisawa S, Schmidt RJ: Diversity and similarity among recognition sequences of Dof transcription factors. Plant J 17: 209-14 (1999).

49. Zhou DX, Li YF, Rocipon M, Mache R: Sequence-specific interaction between S1F, a spinach nuclear factor, and a negative cis-element conserved in plastid-related genes. J Biol Chem 267: 23515-9 (1992).

Figure 5I

SEQ ID No: 35 and SEQ ID NO: 36

```
   1 gaagctgccgtggtcgcagataatgcaattgcaatgctgaggtttctctgagaggatcgatagtcgggac
  71 gattttctctgtttcgatacatatcctttcgcttttcaacgatatcgcttcgttttcagccatttaattc
 141 gcatacgtgaacgaagatcggccgcagtgaaggttatcttgtcgatttcgctgttgtgagcttttgcac
 211 tgcgataacacaccaataggtgtcacttcgctttcattcacgaggtattgaggttgcttctgcttaaaat
 281 ttgatgcgcgagggttttggaaaggcgccagccatgggacggaagcagaaatgcgctgggttcaacaacg
 351 ctggaaaagatttcaacggctttATGTTCCTTGCGGCGTTTATCACTGCTGGTTTTCTTTTCAGCTCTGT
                         M  F  L  A  A  F  I  T  A  G  F  L  F  S  S  V  16
 421 TATTGCTGCAGAAGAAGCAGCAAAGTTAGGAACAGTAATTGGTATAGATCTCGGAACCACGTATTCTTGT
      I  A  A  E  E  A  A  K  L  G  T  V  I  G  I  D  L  G  T  T  Y  S  C  39
 491 GTTGGTGTTTACAAAAATGGTCATGTTGAAATCATAGCAAATGACCAAGGAAATAGGATTACACCTTCTT
      V  G  V  Y  K  N  G  H  V  E  I  I  A  N  D  Q  G  N  R  I  T  P  S  62
 561 GGGTTGCCTTCACTGATACCGAAAGACTCATCGGAGAGGCTGCCAAAAACCAGGCGGCAATGAATCCTGA
      W  V  A  F  T  D  T  E  R  L  I  G  E  A  A  K  N  Q  A  A  M  N  P  E 86
 631 AAGGACCGTTTTTGATGTGAAACGGTTGATTGGAAGAAAGTATGAGGACAAGGAGGTGCAAAAAGACATC
      R  T  V  F  D  V  K  R  L  I  G  R  K  Y  E  D  K  E  V  Q  K  D  I  109
 701 AAACTTTTGCCCTACAAAATTGTAAACAAAGATGGGAAGCCTTACATTCAGGTGAAGATCAGGGATGGTG
      K  L  L  P  Y  K  I  V  N  K  D  G  K  P  Y  I  Q  V  K  I  R  D  G  132
 771 AAATCAAAGTTTTTAGTCCCGAGGAAATTAGTGCAATGATTTTGTTGAAAATGAAGGAAACAGCTGAGTC
      E  I  K  V  F  S  P  E  E  I  S  A  M  I  L  L  K  M  K  E  T  A  E  S 156
 841 CTACCTTGGAAGGAAAAATCAAGGATGCAGTTGTTACAGTTCCAGCATATTTCAATGATGCACAAAGACAG
      Y  L  G  R  K  I  K  D  A  V  V  T  V  P  A  Y  F  N  D  A  Q  R  Q  179
 911 GCCACCAAGGATGCTGGTGTAATTGCTGGGTTAAATGTTGCTCGTATAATAAATGAGCCAACTGCTGCAG
      A  T  K  D  A  G  V  I  A  G  L  N  V  A  R  I  I  N  E  P  T  A  A  202
 981 CAATTGCATATGGTTTGGATAAAAAGGGAGGAGAAAAGAACATTCTTGTTTATGACCTTGGAGGTGGAAC
      A  I  A  Y  G  L  D  K  K  G  G  E  K  N  I  L  V  Y  D  L  G  G  G  T 226
1051 TTTTGATGTCAGTATTCTCACCATTGATAATGGTGTTTTTGAAGTGTTGTCAACCAGCGGGGATACTCAT
      F  D  V  S  I  L  T  I  D  N  G  V  F  E  V  L  S  T  S  G  D  T  H  249
1121 TTAGGAGGAGAGGACTTCGATCAACGAGTTATGGATTACTTCATTAAATTGGTCAAGAAAAAACACAACA
      L  G  G  E  D  F  D  Q  R  V  M  D  Y  F  I  K  L  V  K  K  K  H  N  272
1191 AAGATATTAGCAAGGATAACAGAGCTCTTGGCAAACTTAGGAGGGAGTGTGAGAGGGCCAAAAGAGCTCT
      K  D  I  S  K  D  N  R  A  L  G  K  L  R  R  E  C  E  R  A  K  R  A  L 296
1261 GAGCAGCCAGCATCAAGTTCGTGTTGAAATTGAATCACTTTTTGATGGTGTTGATTTTTCAGAACCATTA
      S  S  Q  H  Q  V  R  V  E  I  E  S  L  F  D  G  V  D  F  S  E  P  L  319
1331 ACAAGAGCAAGATTCGAGGAACTCAATATGGACCTCTTCAAGAAAACTCTTGGGCCAGTAAAGAAGGCTC
      T  R  A  R  F  E  E  L  N  M  D  L  F  K  K  T  L  G  P  V  K  K  A  342
1401 TAGATGATGCTAACTTGCAGAAGACTGAAATTAATGAACTTGTGCTTGTTGGAGGAAGTACTCGCATACC
      L  D  D  A  N  L  Q  K  T  E  I  N  E  L  V  L  V  G  G  S  T  R  I  P 366
1471 AAAGGTTCAGCAATTATTGAAGGACTTATTTGATGGCAAGGAGCCTAACAAAGGTGTTAATCCAGATGAA
      K  V  Q  Q  L  L  K  D  L  F  D  G  K  E  P  N  K  G  V  N  P  D  E  389
1541 GCTGTGGCTTATGGGGCTGCTGTTCAGGGTGGTATTCTGAGTGGTGAGGGAGGTGACGAAACAAAAGATA
      A  V  A  Y  G  A  A  V  Q  G  G  I  L  S  G  E  G  G  D  E  T  K  D  412
1611 TTCTTCTATTGGATGTTGCTCCCCTCAGCCTAGGTATAGAAACTGTTGGTGGAGTAATGACCAAACTTAT
      I  L  L  L  D  V  A  P  L  S  L  G  I  E  T  V  G  G  V  M  T  K  L  I  436
1681 TCCGAGGAACACTGTCATTCCAACAAAGAAGTCACAAGTGTTCACAACTTATCAAGATCAGCAAACCACT
      P  R  N  T  V  I  P  T  K  K  S  Q  V  F  T  T  Y  Q  D  Q  Q  T  T  459
1751 GTTTCAATCAAGGTTTATGAAGGAGAGCGGAGTCTTACAAAGGATTGCCGAGAATTAGGCAAATTTGATC
      V  S  I  K  V  Y  E  G  E  R  S  L  T  K  D  C  R  E  L  G  K  F  D  482
1821 TGTCTGGAATCCCTCCAGCTCCTCGTGGTGTGCCACAGATTGAGGTCACCTTTGAGGTTGATGCCAACGG
      L  S  G  I  P  P  A  P  R  G  V  P  Q  I  E  V  T  F  E  V  D  A  N  G 506
1891 TATCCTCAATGTAAGAGCAGAGGACAAGGGCACCAAGAAAAACCGAAAAGATTACCATCACAAATGACAAA
      I  L  N  V  R  A  E  D  K  G  T  K  K  T  E  K  I  T  I  T  N  D  K  529
1961 GGTAGATTGAGCCAGGAAGAAATAGAAAGAATGGTCAAGGAGGCAGAGGAGTTTGCAGAGGAGGATAAGA
      G  R  L  S  Q  E  E  I  E  R  M  V  K  E  A  E  E  F  A  E  E  D  K  552
2031 AAGTGAAGGACAAAATTGATGCGAGGAACAATCCTTGAAACATATGTCTACAACATGAAAAGCACCATTAA
      K  V  K  D  K  I  D  A  R  N  N  L  E  T  Y  V  Y  N  M  K  S  T  I  N 576
2101 TGAGAAGGATAAATTGGCAGATAAAATTGATTCCGAAGACAAGGAGAAGATCGAAACTGCTATCAAAGAA
      E  K  D  K  L  A  D  K  I  D  S  E  D  K  E  K  I  E  T  A  I  K  E  599
2171 GCATTGGAATGGCTTGATGACAACCAGTCGGCTGAGAAGGAGGACTTCGAGGAGAAGTTGAAAGAGGTGG
      A  L  E  W  L  D  D  N  Q  S  A  E  K  E  D  F  E  E  K  L  K  E  V  622
2241 AAGCTGTATGCAGTCCCATCATCAAGCAAGTATATGAGAAAACTGGAGGAGGATCTTCTGGAGGCGATGA
      E  A  V  C  S  P  I  I  K  Q  V  Y  E  K  T  G  G  G  S  S  G  G  D  D  646
2311 TGAAGACGAGGACTCGCATGAAGAACTCtaagccatttcagtttctgttgaattttagttgtacaaatca
      E  D  E  D  S  H  E  E  L                                              655
2381 cgatgaactaattctacagaagagatctctgagcataataggggtttatgaggatgattggcaacgaacaa
2451 gagattcaactgatgaaagtcaaatgatgtttgtttttctatcaatcagaatgttattttcacagatt
2521 gaaattggcaacgaacaagagattcaactgatgaaagtcaaatgactatttgtttgttttttctatcaat
2591 cagaatgttattttcacagatttttcaatctgtagt
```

PLANT PROMOTER DERIVED FROM LUMINAL BINDING PROTEIN GENE AND METHODS FOR ITS USE

FIELD

This invention relates to an isolated luminal binding protein promoter sequence and methods for its use.

BACKGROUND

Molecular Chaperone Proteins

Luminal binding proteins (BiP) have been identified as a type of molecular chaperone localized within the endoplasmic reticulum (ER) and nuclear envelope of eukaryotic cells. BiP is a member of the heat-shock protein 70 (HSP70) family of proteins (Haas, *Experimentia* 50:1012–1020, 1994). BiP has been found to assist in the co-translational translocation of newly synthesized polypeptides across the ER membrane in yeast (Vogel et al., *J. Cell Biol.* 110:1885–1895, 1990; and Nguyen et al., *Proc. Natl. Acad Sci. USA* 88:1565–1569, 1991). BiP remains associated with polypeptides until they attain their properly folded conformation and/or subunit assembly. For polypeptides that are unable to attain their mature conformation due to misfolding (Schmitz et al., *EMBO J.* 14:1091–1098, 1995) or lack of a subunit component (Knittler et al., *Proc. Natl. Acad Sci. USA* 92:1764–1768, 1995), BiP remains associated with the polypeptide until the polypeptide is degraded.

In angiosperms, the expression of BiP is subject to developmental, hormonal, stress-induced, and diurnal regulation (Denecke et al., *Plant Cell* 3:1025–1035, 1991; Jones et al., *Plant Physiol.* 97:456–459, 1991; Anderson et al., *Plant Physiol.* 104:1359–1370, 1994; Kalinski et al., *Planta* 195:611–621, 1995; and Figueiredo et al., *Braz. J. Plant Physiol.* 9:103–110, 1997). BiP associates with the bean storage protein phaseolin (D'Amico et al., *Plant J.* 2:443–455, 1992; Pedrazzini et al., *Plant J.* 5:103–110, 1994) and with rice prolamines (Li et al., *Science* 262:1054–1056, 1993). High levels of BiP expression are associated with the accumulation of protein intermediates that are unable to attain their proper folded conformation because of mutations such as those seen in the maize zein regulatory mutants "floury-2," "defective endosperm-B30," and "mucronate" (Boston et al., *Plant Cell* 3:497–505, 1991; Fontes et al., *Plant Cell* 3:483–496, 1991).

Treatment with tunicamycin, which inhibits N-linked glycosylation and proper protein folding, also results in increased levels of BiP expression (Denecke et al., *Plant Cell* 3:1025–1035, 1991; and D'Amico et al., *Plant J.* 2:443–455, 1992). However, the increased expression resulting from unfolded proteins and from increased levels of secretory protein traffic may be mediated through different signals (Pahl et al., *EMBO J.* 14:2580–2588, 1995).

SUMMARY

The invention provides a Douglas-fir (*Pseudotsuga menziesii*) luminal binding protein promoter (PmBiPPro1; SEQ ID NO: 31). Expression of the PmBiP protein (SEQ IDNO: 36) is shown herein to be developmentally-regulated and inducible by environmental changes. The promoter (PmBiPPro1; SEQ ID NO: 31), fragments thereof, and variants thereof are useful for expressing heterologous proteins either transiently in host cells or transgenically in stably transformed cells and plants.

One aspect of the invention provides the PmBiP promoter (SEQ ID NO: 31), fragments/deletions of the PmBiP promoter (SEQ ID NO: 31) and variants thereof. The variant promoters are characterized by their retention of at least 50% sequence identity with the disclosed promoter sequences (SEQ ID NOS: 16, 17, 18, and 31, respectively), or by their retention of at least 20, 30, 40, 50, or 60 consecutive nucleic acid residues of the disclosed promoter sequences (SEQ ID NOS: 16, 17, 18, and 31). In each case these promoters, at a minimum, retain promoter activity. In some cases these promoters retain native PmBiP promoter activity.

It is also contemplated that promoters such as the CaMV35S promoter may be altered through the introduction of sequences found in the PmBiP promoter (SEQ ID NO: 31). The resulting promoter also will be characterized by its retention of at least 20, 30, 40, 50, or 60 consecutive nucleic acid residues of the disclosed promoter sequences (SEQ ID NOS: 16, 17, 18, and 31).

Another aspect of the invention provides vectors containing the above-described promoters and variants thereof. The vectors can be transformed into host cells. If the host cell is a plant cell, the transformed host cell can give rise to a transgenic plant.

The invention also provides transgenes. These transgenes include one of the above-described promoter sequences operably linked to one or more open reading frames (ORFs). The transgenes can be cloned into vectors and subsequently used to transform host cells such as bacterial, insect, mammalian, fungal, yeast, or plant cells.

Accordingly, the invention provides transgenic plants such as maize, wheat, rice, millet, tobacco, sorghum, rye, barley, brassica, sunflower, seaweeds, lemna, oat, soybean, cotton, legumes, rape/canola, alfalfa, flax, sunflower, safflower, brassica, cotton, flax, peanut, and clover; lettuce, tomato, cucurbits, cassava, potato, carrot, radish, pea, lentil, cabbage, cauliflower, broccoli, Brussel sprouts, peppers and other vegetables; citrus, apples, pears, peaches, apricots, walnuts, and other fruit trees; orchids, carnations, roses, and other flowers; cacao; poplar, elms, and other deciduous trees; pine, Douglas-fir, spruce, and other conifers; turf grasses; cacao; and rubber trees and other members of the genus Hevea.

In yet another embodiment, the invention provides methods for expressing proteins in host cells, such as plant host cells. Such methods involve operably linking a promoter, such as those described above, to at least one ORF to produce a transgene, and introducing the transgene into a plant. Accordingly, the invention also provides proteins that are produced by these methods.

The PmBiP promoter (SEQ ID NO: 31) is shown herein to be inducible (at least via wounding and probably via cold temperatures), and the amount of mRNA encoding PmBiP protein as well as BiP protein itself has been shown to be increased at cold temperatures, thus making the PmBiP promoter ideal for use in the expression of proteins. This is because cold temperatures serve to stabilize the protein during translation. Accordingly, another aspect of the invention provides inducible promoters derived through the use of fragments of the promoter described herein.

An alternative method of characterizing promoters is by analyzing the various promoter elements found within a promoter sequence. Hence, the invention also provides promoters that maintain promoter activity and include at least 8 promoter elements selected from the group consisting of the E-box motif (SEQ ID NO: 1), the MNF1 element (SEQ ID NO: 28), the POLLEN1LELAT52 element (SEQ ID NO: 29), the ROOTMOTIF element (SEQ ID NO: 30), the 2SSEEDPROTBANAP element (SEQ ID NO: 32), the BOXIIPCCHS element (SEQ ID NO: 33), the ASF1 MOTIF element (SEQ ID NO: 34), ACGT-core elements (SEQ ID NO: 4), the CAAT-box (SEQ ID NO: 9), the CANABN-NAPA element (SEQ ID NO: 12), the HEXMOTIF element (SEQ ID NO: 27), and duplicates thereof, wherein the promoter displays promoter activity. The invention also provides promoters that contain the following promoter elements in the following orientation: 3'-ACGT-core element (SEQ ID NO: 4), E-box motif (SEQ ID NO: 1), CAAT-box (SEQ ID NO: 9), 2SSEEDPROTBANAP (SEQ ID NO: 32), CANABNNAPA element (SEQ ID NO: 12), HEXMOTIF element (SEQ ID NO: 27), CAAT-box (SEQ ID NO: 9), BOXIIPCCHS element (SEQ ID NO: 33), E-box motif (SEQ ID NO: 1), ASF1MOTIF (SEQ ID NO: 34), POLLEN1LELAT52 element (SEQ ID NO: 29), and MNF1 element (SEQ ID NO: 28) -5'.

Finally, the invention also provides vectors, host cells, and transgenic plants that include the promoters described above by their inclusion of various promoter elements.

These and other aspects of the invention will become readily apparent from the following detailed description.

BRIEF DESCRIPTION OF THE FIGURES

FIGS. 5A–5I are a table of cis-acting elements located in the PmBiP promoter (SEQ ID NO: 31) using the plant cis-acting regulatory database (PLACE; Higo et al, *Plant Mol. Biol. Rep.* 5:387–405. 1987; and Prestridge, *CABIOS* 7:203–206, 1991). Cis elements are grouped according to type. Elements deleted from PmBiPPro1-1 construct to form PmBiPPro1-3 are darkly shaded, elements deleted from PmBiPPro1-3 construct to form PmBiPPro1-5 are lightly shaded, and elements remaining in the PmBiPPro1-5 construct are not shaded.

FIG. 10 is the nucleotide and deduced amino acid sequence of PmBiP cDNA. The nucleotide sequence is numbered on the left, and the amino acid sequence is numbered on the right. Untranslated regions are in lower-case letters and the open reading frame is capitalized. The three potential start codons are underlined, with the amino acid sequence beginning at the 3rd codon. The predicted signal-peptide cleavage site and beginning of the mature PmBiP amino acid sequence is indicated by an asterisk (Nielsen et al., *Protein Eng.* 10:1–6, 1997). The ER-retention signal sequence is boxed. The 13 carboxy-terminal amino acids used to generate an antiserum to the peptide are indicated in bold italics.

SEQUENCE LISTING

Figure 1:
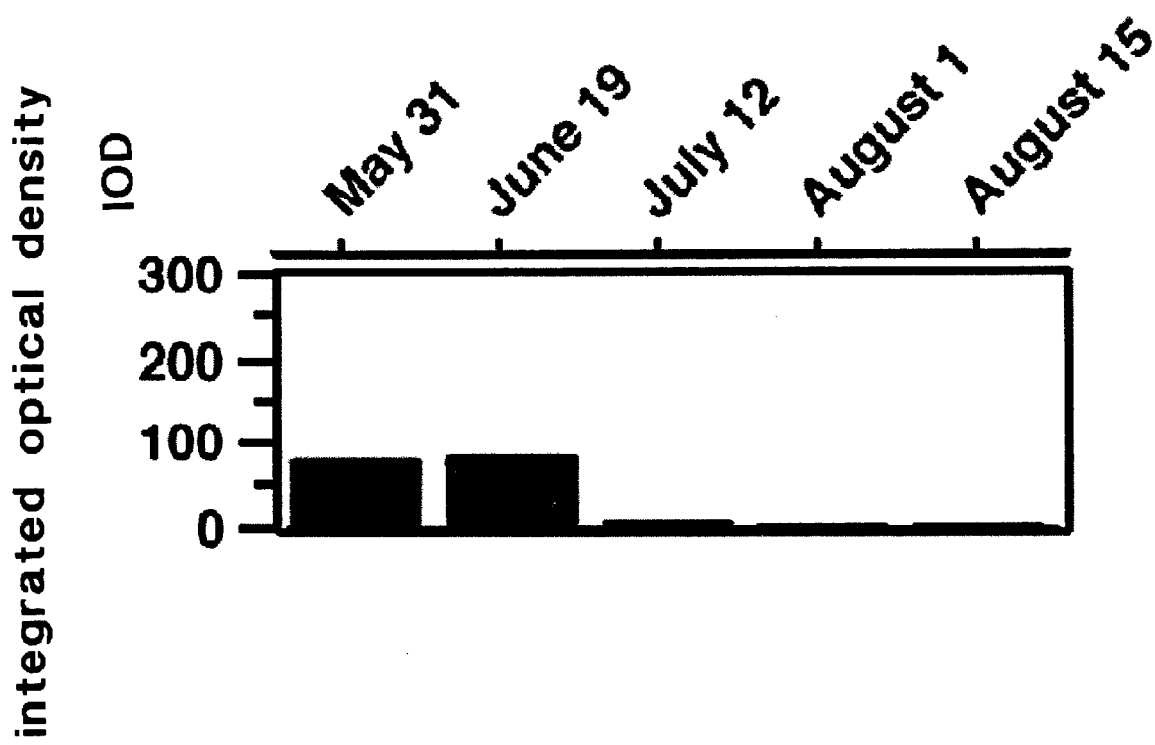
FIG. 1 is a graph depicting the expression of PmBiP protein during Douglas-fir seed development. Total RNA was isolated from whole developing seeds collected at the indicated time points and subjected to northern blot analysis (20 μg per lane) using the PmBiP cDNA as probe. The indicated time points correspond to the following developmental stages, based on morphological characteristics of embryos established by Allen and Owens (Allen and Owens, *The Life History of Douglas-fir*, Environment Canada, Canadian Forestry Service, Ottawa, 1972): May 31—prefertilization, June 19—proembryo, July 12—early to mid-cotyledonary embryo, August 1—mid to late embryo, August 15—late to mature embryo. The same membrane was stripped and re-probed with a genomic DNA probe encoding the Douglas-fir 18S rRNA subunit to account for differences in the amount of RNA loaded per lane. Differences in the amount of PmBiP transcript were adjusted for differences in the amount of RNA loaded per lane (given in units of integrated optical density).

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 is the nucleic acid sequence of an E-box motif.

SEQ ID NO: 2 is the nucleic acid sequence of a RY-repeated element.

SEQ ID NO: 3 is the nucleic acid sequence of an AT-rich region.

SEQ ID NO: 4 is the nucleic acid sequence of an ACGT-core element.

SEQ ID NO: 5 is the nucleic acid sequence of an opaque-2-like binding site.

SEQ ID NOs: 6 and 7 are the nucleic acid sequences of respective conserved gymnosperm-like regions.

SEQ ID NO: 8 is the nucleic acid sequence of a TATA box.

SEQ ID NO: 9 is the nucleic acid sequence of a CAAT box.

SEQ ID NO: 10 is the nucleic acid sequence of a MYBPZM element.

SEQ ID NO: 11 is the nucleic acid sequence of a GT1 consensus sequence.

SEQ ID NO: 12 is the is the nucleic acid sequence of a CANBNAPA element.

SEQ ID NO: 13 is the nucleic acid sequence of a MARARS element.

SEQ ID NOS: 14 and 15 are specific examples of opaque-2-like binding sites.

SEQ ID NO: 16 is the nucleic acid sequence of the PmBiPPro1-1 promoter construct.

SEQ ID NO: 17 is the nucleic acid sequence of the PmBiPPro1-3 construct.

SEQ ID NO: 18 is the nucleic acid sequence of the PmBiPPro1-5 construct.

SEQ ID NOS: 19–22 are respective PCR primers used in inverse-PCR reactions.

SEQ ID NOS: 23–26 are respective PCR primers used to clone the PmBiP promoter.

SEQ ID NO: 27 is the nucleic acid sequence of a HEXMOTIF element.

SEQ ID NO: 28 is the nucleic acid sequence of a MNF1 element.

SEQ ID NO: 29 is the nucleic acid sequence of a POLLEN1LELAT52 element.

SEQ ID NO: 30 is the nucleic acid sequence of a ROOTMOTIF element.

SEQ ID NO: 31 is the complete PmBiP promoter sequence.

SEQ ID NO: 32 is the nucleic acid sequence of a 2SSEEDPROTBANAP element.

SEQ ID NO: 33 is the nucleic acid sequence of a BOXIIPCCHS element.

SEQ ID NO: 34 is the nucleic acid sequence of an ASF1MOTIF.

SEQ ID NO: 35 is the cDNA sequence encoding the luminal binding protein BiP.

SEQ ID NO: 36 is the amino acid sequence of the luminal binding protein.

SEQ ID NO: 37 is the amino acid sequence of the endoplasmic reticulum (ER) retention sequence, HEEL.

DETAILED DESCRIPTION

I. Definitions

Unless otherwise noted, technical terms are used according to conventional usage. Definitions of common terms in molecular biology may be found in Lewin, *Genes VII*, Oxford University Press, 1999 (ISBN 0-19-879276-X); Kendrew et al. (eds.), *The Encyclopedia of Molecular Biology*, Blackwell Science, Ltd., 1994 (ISBN 0-632-02182-9); and Meyers (ed.), *Molecular Biology and Biotechnology. A Comprehensive Desk Reference*, VCH Publishers, Inc., 1995 (ISBN 1-56081-569-8).

In order to facilitate review of the various embodiments of the invention, the following definitions are provided:

"cDNA (complementary DNA)." A "cDNA" is a piece of DNA lacking internal, non-coding segments (introns) and transcriptional regulatory sequences. cDNA also may contain untranslated regions (UTRs) that are responsible for translational control in the corresponding RNA molecule. cDNA usually is synthesized in the laboratory by reverse transcription from messenger RNA extracted from cells.

"Cationic Peptides." "Cationic peptides" are endogenous antimicrobial peptides produced by plants and animals typically consisting of 12–45 amino acids. Additionally, they are amphipathic molecules having a net positive charge (cationic) at physiological pH. Although cationic antimicrobial peptides (CAPs) are structurally diverse, they fall into two general classes of structures: α-helical peptides, such as the cecropins and magainans, and β-sheet peptides stabilized by intramolecular disulphide bonds, such as the defensins, protegrins, and tachyplesins. Hancock and Lehrer, *Trends Biotechnol.* 16:82–88, 1998; Zasloff, *Curr. Opin. Immunol.* 4:3–7, 1992; Cociancich et al., *Biochem. J.* 300:567–575 1994; and Piers and Hancock, *Mol. Microbiol.* 12:951–958, 1994. Natural CAPs vary greatly in their respective spectra of biological activities, including killing bacteria (Gram-positive and -negative), fungi, protozoa, and viruses. CAPs normally kill susceptible microorganisms in vitro at concentrations from 0.25 μg/ml to 4 μg/ml (Hancock and Lehrer, *Trends Biotechnol.* 16:82–88, 1998), providing exciting possibilities in the face of the declining efficacy of conventional antibiotics. Furthermore, the expression of CAP in plants may introduce broad-spectrum resistance to phytopathogenic microorganisms. Jaynes, *Plant Science* 89:43–53, 1993; and Misra and Zhang, *Plant Physiol.* 106:977–981, 1994.

Cationic peptides are one type of protein that might be expressed under the control of the disclosed PmBiP promoter (SEQ ID NO: 31). Other proteins that confer disease resistance, resistance to environmental stress, resistance to insect infestation, or herbicide resistance, or alter consumer-related characteristics such as shelf-life, color, or nutritional value, also may be expressed under the control of the PmBiP promoter (SEQ ID NO: 31) described herein.

"Deletion." A "deletion" is the removal of one or more nucleic acid residues from a DNA sequence, the regions on either side of the removed sequence being joined together.

"Douglas-fir luminal binding protein promoter (PmBiPPro1)." The nucleic acid sequence of the PmBiP promoter is provided in SEQ ID NO: 31. However, the invention also encompasses variants and fragments of the PmBiP promoter (SEQ ID NO: 31) that are characterized by their ability to maintain promoter activity, at a minimum, and in some cases maintain native PmBiP promoter activity. These variants have at least 50%, 60%, 70%, 80%, or 90% sequence identity when compared to the nucleic acid sequences shown in SEQ ID NOS: 16, 17, 18, and 31. These variants can be isolated from nature using the hybridization or PCR techniques described below, or they can be made by manipulating the nucleic acid sequences shown in SEQ ID NOS: 16, 17, 18, and 31.

The PmBiP promoter shown in SEQ ID NO: 31 contains several distinct promoter elements and inter-element spaces that are arranged in series in the DNA fragment. One or more of these elements or inter-element spaces can be altered, deleted, and/or duplicated without loss of promoter activity. Also, one of ordinary skill in the art will appreciate other promoter elements may be added to the promoter shown in SEQ ID NO: 31 without loss of promoter activity and/or native PmBiP promoter activity. Hence, the invention provides promoters that maintain native promoter activity and/or promoter activity and include at least 10, 12, 14, 16, 18, 20, 22, 30, or 35 of the promoter elements contained within the PmBiP promoter (SEQ ID NO: 31).

Variants of the PmBiP promoter also can be characterized by the number of contiguous nucleic acid residues they share with the PmBiP promoter (SEQ ID NO: 31). For example, a variant of the PmBiP promoter can share at least 20, 25, 30, 40, 50, or 60 contiguous nucleic acid residues with the PmBiP promoter shown in SEQ ID NO: 31. Such variants additionally will be characterized by their ability to drive the expression of a transgene operably linked to it.

"Insertion." An "insertion" is the addition of one or more nucleotide or amino acid residues into a nucleic acid sequence or an amino acid sequence, respectively.

"Isolated." An "isolated" biological component (such as a nucleic acid, protein, or organelle) has been substantially separated or purified from other biological components in the cell of the organism in which the component naturally occurs, i.e., other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

"Native PmBiP Promoter Activity." "Native PmBiP promoter activity" is characterized by developmental-specific transcription. mRNA encoding the PmBiP protein has been shown to be expressed in seeds, following stratification and exposure to germination conditions, to a greater extent than in mature seeds. Hence, it is believed that the PmBiP promoter (SEQ ID NO: 31) will drive the expression of transgenes in a similar pattern. Developmental-specific activity is defined as the ability of a promoter to drive transcription at a higher level during one stage in development compared to another stage of development.

Furthermore, developmental-specific expression can be determined by creating transgenic plants and assaying the resulting transgenic tissues (e.g., leaves, flowers, seeds, roots) for transgene mRNA or by assaying for a reporter gene such as GUS. Developmental-specific expression is quantified by comparing the level of mRNA expressed in a tissue during one stage in development compared to the level expressed in the same tissue at another stage of development. The degree of developmental-specific expression is expressed in terms of a percentage of expression, i.e., the percentage of mRNA in one developmental stage compared to another. For example 100% (1×) expression denotes that an equal amount of expression is observed during two distinct stages of development, 200% (2×) denotes that twice as much mRNA is expressed in one tissue compared to another tissue. Native PmBiP promoter activity is, therefore, defined by the ability of the PmBiP promoter to drive the expression of mRNA to a greater degree during one stage in plant development compared to another stage in development (i.e., at least 101%). Of course, the PmBiP promoter (SEQ ID NO: 31) can show an even stronger bias for developmental-specific expression, such as at least 125%, 150%, 200%, 250%, or 300% developmental-specific expression in seeds.

"Oligonucleotide ("oligo")." An "oligonucleotide" refers to a linear polynucleotide sequence of up to about 100 nucleotide bases in length.

"Open reading frame (ORF)." An "open reading frame" is a series of nucleotide triplets (codons) coding for amino acids without any internal termination codons. These sequences are usually translatable into a peptide.

"Operably linked." A first nucleic acid sequence is "operably linked" with a second nucleic acid sequence whenever the first nucleic acid sequence is situated in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, are in the same reading frame.

"Orthologs." "Orthologs" are nucleic acid or amino acid sequences that share a common ancestral sequence, but that diverged when a species carrying that ancestral sequence split into two species. Orthologous sequences are usually also homologous sequences.

"Probes and primers." Nucleic acid "probes and primers" readily may be prepared based on the nucleic acid sequences provided by this invention. A "probe" comprises an isolated nucleic acid sequence attached to a detectable label or reporter molecule. These labeled nucleic acid sequences are useful for identifying other promoters and seed-storage proteins. Typical labels include radioactive isotopes, ligands, chemiluminescent agents, and enzymes. Methods for labeling and guidance in the choice of labels appropriate for various purposes are discussed, e.g., in Sambrook et al. (eds.), *Molecular Cloning: A Laboratory Manual*, 2nd ed., vol. 1-3, Cold Spring Harbor Laboratory Press, Cold Spring Harbor, N.Y., 1989; and Ausubel et al. (ed.), *Current Protocols in Molecular Biology*, Greene Publishing and Wiley-Interscience, New York (with periodic updates), 1987.

"Primers" are short nucleic acids, preferably DNA oligonucleotides 15 nucleotides or more in length, that can be annealed to a complementary target DNA strand by nucleic acid hybridization to form a hybrid between the primer and the target DNA strand. The annealed primers can be extended along the target DNA strand by a DNA polymerase enzyme. Primer pairs can be used for amplification of a nucleic acid sequence, e.g., by the polymerase chain reaction (PCR) or other nucleic-acid amplification methods known in the art.

As noted, probes and primers are preferably 15 nucleotides or more in length, but, to enhance specificity, probes and primers of 20 or more nucleotides may be preferred.

Methods for preparing and using probes and primers are described, for example, in Sambrook et al. (eds.), *Molecular Cloning: A Laboratory Manual*, 2nd ed., vol. 1-3, Cold Spring Harbor Laboratory Press, Cold Spring Harbor, N.Y., 1989; Ausubel et al. (eds.), *Current Protocols in Molecular Biology*, Greene Publishing and Wiley-Interscience, New York (with periodic updates), 1987; and Innis et al., *PCR Protocols: A Guide to Methods and Applications*, Academic Press: San Diego, 1990. PCR primer pairs can be derived from a known sequence, for example, by using computer programs intended for that purpose such as Primer™ (Version 0.5, 1991, Whitehead Institute for Biomedical Research, Cambridge, Mass.). One of skill in the art will appreciate that the specificity of a particular probe or primer increases with the length of the probe or primer. For example, a primer comprising 20 consecutive nucleotides will anneal to a target with a higher specificity than a corresponding primer of only 15 nucleotides. Thus, in order to obtain greater specificity, probes and primers may be selected that comprise, by way of example, 10, 20, 25, 30, 35, 40, 50 or more consecutive nucleotides.

"Promoter Activity." "Promoter activity" is defined as the ability of a DNA sequence to drive transcription. Promoter activity varies with the number and position of the promoter elements. For example, the PmBiP promoter (SEQ ID NO: 31) can be altered to remove its developmental-specific activity (native activity) without loss of its ability to drive transcription.

"Promoter elements." "Promoter elements" as used herein refers to sub-domains within the promoter that confer tissue-specific expression, enhance expression, or inhibit expression. A promoter can contain multiple promoter elements. Furthermore, some elements can appear more than once within a single promoter. Examples of such elements are E-box motifs (SEQ ID NO: 1), RY-repeat elements (SEQ ID NO: 2), AT-rich regions (SEQ ID NO: 3), ACGT-core elements (SEQ ID NO: 4), Opaque-2-like elements (SEQ ID NO: 5), and conserved gymnosperm-like regions (SEQ ID NOS: 6 and 7). Additional examples of promoter elements can be found in U.S. Patent Nos: U.S. Pat. No. 5,723,751 to Chua; U.S. Pat. No. 5,608,149 to Barry et al.; U.S. Pat. No. 5,589,615 to De Clercq et al.; U.S. Pat. No. 5,589,583 to Klee et al.; U.S. Pat. No. 5,677,474 to Rogers; U.S. Pat. No. 5,487,991 to Vandekerckhove et al.; and U.S. Pat. No. 5,530,194 to Knauf et al. Typically, a TATA box is found on the 3'-end of the series of promoter elements.

Examples of specific promoter elements are provided above and in the sequence listing. However, one of skill in the art will appreciate that the specific examples shown in the sequence listing can be modified while still maintaining activity. For example a base in an RY-repeat element can be altered by the substitution of one or more acid residues without the RY-repeat element losing its functionality within the overall promoter sequence.

After a promoter has been identified, the promoter elements can be characterized, such as is described below for the PmBiP promoter (SEQ ID NO: 31; FIG. 5). This promoter contains a series of identifiable promoter elements. These elements appear in series in the genomic DNA as is shown schematically in FIG. 6. The space between the elements is hereinafter referred to as "inter-element space." An inter-element space can be modified through the addition, deletion, and/or substitution of nucleotides without loss of promoter activity.

The PmBiP promoter (SEQ ID NO: 31) also can be modified by deleting elements from the promoter and/or duplicating elements within the promoter. One of ordinary skill in the art will appreciate that such modifications to the promoter can enhance promoter activity, inhibit promoter activity, or alter the level of tissue-specific expression of the promoter.

One of skill in the art will appreciate that, by modifying the order of the promoter elements, the number of the promoter elements, and/or the length of the inter-element space(s), one can modify promoter activity and/or native PmBiP promoter activity. However, in each case, the PmBiP promoter (SEQ ID NO: 31) will be capable of driving the expression of the gene operably linked to it. Assays for quantifying PmBiP activity as well as native PmBiP activity are provided below.

"Protein." A biological molecule expressed by a gene and comprised of amino acids.

"Purified." The term "purified" does not require absolute purity; rather, it is intended as a relative term. Thus, for example, a purified protein preparation is one in which the protein referred to is purer than the protein in its natural environment within a cell or within a production reaction chamber (as appropriate).

"Recombinant." A "recombinant" nucleic acid is one having a sequence that does not occur naturally or having a sequence made by an artificial combination of two otherwise separated sequences. This artificial combination is often accomplished by chemical synthesis or, more commonly, by the manipulation of isolated segments of nucleic acids, e.g., by genetic engineering techniques.

"Sequence identity." The term "sequence identity" is used to describe the similarity between two nucleic acid sequences or between two amino acid sequences. Sequence identity is typically expressed in terms of percentage identity; the higher the percentage, the more similar the two sequences.

Methods for aligning sequences for comparison purposes are well-known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444–2448, 1988; Higgins and Sharp, *Gene* 73:237–244, 1988; Higgins and Sharp, *CABIOS* 5:151–153, 1989; Corpet et al., *Nucl. Acids Res.* 16:10881–10890, 1988; Huang et al., *Comput. Applic. Biosciences* 8:155–165, 1992; and Pearson et al., *Meth. Mol. Biol.* 24:307–331, 1994. Altschul et al., *J. Mol. Biol.* 215:403–410, 1990, presents a detailed discussion of sequence-alignment methods and homology calculations.

The NCBI Basic Local Alignment Search Tool (BLAST™, Altschul et al. *J. Mol. Biol.* 215:403–410, 1990) is available from several sources, including the National Center for Biotechnology Information (NCBI, Bethesda, Md.) and on the Internet, for use in connection with the sequence-analysis programs blastp, blastn, blastx, tblastn and tblastx. BLAST™ can be accessed at the web site maintained by the NCBI. A description of how to determine sequence identity using this program is also available at the same web site.

For comparisons of amino acid sequences of greater than about 30 amino acids, the "Blast 2 sequences" function in the BLAST™ program can be employed using the default BLOSUM62 matrix set to default parameters, (gap existence cost of 11, and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins having even greater similarity to the reference sequences will show increasing percentage identities when assessed by this method, such as at least 45%, at least 50%, at least 60%, at least 70%, at least 75%, at least 80%, at least 85%, at least 90%, or at least 95% sequence identity.

A first nucleic acid is "substantially similar" to a second nucleic acid if, when optimally aligned (with appropriate nucleotide insertions or deletions) with the other nucleic acid (or its complementary strand), nucleotide-sequence identity occurs in at least about 60%, 75%, 80%, 85%, 90% or 95% of the nucleotide bases. (As used herein, "optimally aligned" sequences exhibit a maximal possible sequence identity). Sequence similarity can be determined by comparing the nucleotide sequences of two nucleic acids using the BLAST™ sequence-analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if it shows sequence identity of at least about 75%–90% or greater when optimally aligned and compared using BLAST™ software (blastp) using default settings.

"Transformed." A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, and introduction of naked DNA by electroporation, lipofection, and particle gun acceleration.

"Transgenic plant." As used herein a "transgenic plant" refers to a plant that contains recombinant genetic material ("transgene") normally not found in a wild-type plant of the same species. Thus, a plant that is grown from a plant cell into which recombinant DNA is introduced by transformation is a transgenic plant, as are all offspring of that plant containing the introduced transgene (whether produced sexually or asexually).

"Vector." A "vector" is a nucleic acid molecule as introduced into a host cell, thereby producing a transformed host cell. A vector may include one or more nucleic acid sequences, such as an origin of replication, that permit the vector to replicate in a host cell. A vector also may include one or more selectable marker genes and other genetic elements known in the art.

Unless otherwise defined, all technical and scientific terms used herein have the same respective meanings as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

II. Assessment of Promoter Activity

A. Experimental Overview

A cDNA encoding the Douglas-fir luminal binding protein (PmBiP) was isolated by screening a Douglas-fir CDNA library with a previously isolated partial PmBiP cDNA clone. Four potential clones were isolated. The nucleotide and deduced amino acid sequence of the largest cDNA clone (PmBiP3) were used in subsequent experiments showing that PmBiP protein expression is developmentally and environmentally regulated. More specifically, PmBiP RNA levels to increased upon exposure to cold temperature, before and after fertilization and during germination.

The promoter responsible for the expression of the PmBiP protein was isolated by extracting genomic DNA from Douglas-fir spring-flush needles. The genomic DNA was then digested with either XbaI or SacI, re-circularized, subjected to PCR amplification, and identified via Southern blotting with a probe generated from a PmBiP CDNA clone.

Constructs containing the full-length PmBiP promoter (SEQ ID NO: 31) and deletions thereof then were cloned upstream from the uidA (β-glucuronidase (GUS)) gene, and experiments were designed to determine the activity of the promoter. The PmBiP promoter (SEQ ID NO: 31) as well as the various deletions thereof (SEQ ID NOS: 16, 17, and 18) were highly active. In fact, in some cases, the PmBiP promoter (SEQ ID NO: 31) and fragments thereof were significantly more active than the commonly used 35S CaMV promoter.

B. Materials and Methods Relating to the Expression Pattern of PmBiP

1. Plant Material

Coastal Douglas-fir (*Pseudotsuga menziesii* [Mirb] Franco) seeds (seed-lot #952) were grown as previously described (Tranbarger et al., *Gene* 172:221–226, 1995). Germninating and young seedlings were collected at midday at the times indicated, frozen in liquid nitrogen, and stored at −80° C. until further use. Growth of young Douglas-fir seedlings (high elevation seed-lot #6485) used for seasonal expression analysis was as described in Ekramoddoullah et al., *Can. J. For Res.* 25:1137–1147, 1995. One needle from each of 112 trees was collected. The needles were pooled on the morning of the dates indicated, frozen in liquid nitrogen, freeze dried, ground to a powder, and stored at −20° C. until further use. Developing seeds were collected from an open-pollinated seed orchard during midday on the dates indicated at Pacific Forest Products Ltd., Saanichton, B.C., Canada. Developing seeds were promptly dissected from cones, frozen on dry ice, and stored at −80° C. until further use.

2. Isolation of Full Length BiP cDNA's.

A partial length BiP cDNA clone from a Douglas-fir cDNA library prepared from poly A$^+$ RNA isolated from 4–6-day old seedlings was used as a probe (Tranbarger et al., *Gene* 172:221–226, 1995). The cDNA was $^{32}$P-labelled with a random primers DNA labelling kit (GIBCO BRL, Burlington, Ontario, Canada) and used to re-screen the cDNA library, according to the manufacturer's instructions (Strategene, La Jolla, Calif., USA), to obtain a full-length cDNA. Plasmid DNA from each positive clone was digested with EcoR1 and electrophoresed on a 1% agarose gel. The DNA was transferred to a Zeta Probe™ membrane (BioRad, Mississauga, Ontario, Canada) for Southern blotting. Clones containing a BiP cDNA insert of an appropriate size were selected for DNA sequencing.

3. DNA Sequencing and Analysis

The largest cDNA clone was selected for double-stranded DNA sequencing using Sequenase™ (United States Biochemical, Cleveland, Ohio, USA) and oligo primers synthesized on a PCR MATE™ 391 DNA synthesizer (Applied Biosystems, Mississauga, Ontario, Canada). Prediction of the signal sequence and signal-peptide cleavage site from deduced amino acid sequences was performed using the "SignalP" V1.1 World Wide Web Server (Nielsen et al., *Protein Eng.* 10:1–6, 1997). Amino-acid-sequence alignments were constructed using "CLUSTAL W" v1.7 (Thompson et al., *Nucl. Acids Res.* 22:4673–4680, 1994). The phylogenetic tree was constructed using the PHYLIP package (Felsenstein, *Cladistics* 5:164–166, 1989). The amino acid sequences (and database accession numbers) used for this analysis were: *Aspergillus awamorii* (EMBL: Y12504), *Aplysia californica* (PIR: S24782), *Arabidopsis thaliana* 1 (DDBJ: D89341), *Arabidopsis thaliana* 2 (DDBJ: D89342), *Caenorhabditis elegans* (GENBANK: U56965), *Drosophila melanogaster* (PIR:JN0666), *Echinococcus granulosus* (GENBANK: M63605), *Echinococcus multilocularis* (GENBANK: M63604), *Eimeria tenella* (EMBL: Z66492), *Gallus gallus* (PIR: I50242), *Glycine max A* (GENBANK: U08384), *Glycine max B* (GENBANK: U08383), *Homo sapiens* (SWISS-PROT: P11021), *Lycopersicon esculentum* (SWISSPROT: P49118), *Mesocricetus auratus* (SWISS-PROT: P07823), *Mus musculus* (SWISS-PROT: P20029), *Neurospora crassa* (EMBL: Y09011), *Nicotiana tabacum* 4 (SWISS-PROT: Q03684), *Nicotiana tabacum* 5 (PIR: JQ1361), *Oryza sativa* (GENBANK: AF006825), *Phytophthora cinnamomi* (PIR: S38890), *Plasmodium falciparum* (EMBL: X69121), *Phaeodactylum tri*-

*cornutum* (GENBANK: U29675), *Rattus norvegicus* (SWISS-PROT: P06761), *Saccharomyces cerevisiae* (SWISS-PROT: P16474), *Spinacia oleracea* (GENBANK: L23551), *Trypanosoma brucei* (GENBANK: L14477), *Xenopus laevis* (GENBANK:U62807), *Zea mays E2* (GENBANK: U58208), and *Zea mays E3* (GENBANK: U58209).

4. Genomic DNA Extraction and Restriction Analysis

Douglas-fir genomic DNA was extracted from spring-flush needles by a modification of the "CTAB" method (De Verno et al., *Constructing Conifer Genomic Libraries: A Basic Guide*, Information Report, Petawawa National Forestry Institute, Canadian Forest Service, PI-X-88, 1989). Aliquots of 10 µg of DNA were digested for 26 hours with restriction enzymes, then separated on a 0.7% agarose gel. Hybridization methods were based on those described in Lueders and Fewell, *Biotechniques* 16:66–67, 1994, as follows: The gel was incubated at room temperature with shaking in denaturing solution (0.5 N NaOH, 150 mM NaCl) for 30 minutes, rinsed in distilled water, and incubated in neutralizing solution (500 mM Tris-HCl pH 8, 150 mM NaCl) for 30 minutes. The gel was dried on a vacuum gel drier for 30 minutes with vacuum only, followed by 1 hour at 60° C. The dried gel (unblot) was probed with $^{32}$P-labelled, random primed, PmBiP CDNA in hybridization solution (0.5 M $Na_2HPO_4$ pH 7.2, 7% SDS, 100 µg/ml denatured salmon sperm DNA) at 65° C. overnight, then washed at low stringency twice in hybridization solution for 45 minutes each at 65° C. The unblot was exposed for 7 days under a phosphor-imaging screen and developed using the STORM 820™ Phosphorimager (Molecular Dynamics, Sunnyvale, Calif., USA). Following development, the unblot was washed at high stringency twice in wash buffer (20 mM $Na_2HPO_4$ pH 7.2, 1% SDS) for 45 minutes each at 65° C. and exposed for 8 days and developed as above. Quantification was performed using the Image Quant NT™ software (Molecular Dynamics). Calculation of gene copy number was as described in Pasternak, Glick, and Thompson (eds.), *Methods in Plant Molecular Biology and Biotechnology*, CRC Press, Inc., Boca Raton, Fla., USA, pp. 29–36, 1993, using a Douglas-fir genome size of 25 µg per haploid nucleus (Ingle et al., *Plant Physiol.* 55:496–501, 1975).

5. Northern Blotting

Total RNA was isolated as described in Kaukinen et al., *Plant Mol. Biol.* 30:1115–1128, 1996, separated on a 1% agarose/formaldehyde gel, and transferred to a Zeta-Probe GT membrane (BioRad, Mississauga, Ontario, Canada). Blots were then probed with $^{32}$P-labelled, random primed, PmBiP CDNA following the basic hybridization conditions described in the Zeta-Probe manual. Blots were stripped and re-probed with a PCR-amplified genomic fragment representing the Douglas-fir 18S rRNA gene to account for differences in the amount of RNA loaded per lane. Densitometry and adjustment for differences in the amount of RNA loaded per lane (calculation of integrated optical density) were performed as described in Tranbarger and Misra, *Physiol. Plant* 95:456–464, 1996. Densitometry for these figures was performed using the ChemiImager™ 4000 system (Alpha Innotech Corporation, San Leandro, Calif., U.S.A.).

6. Antibody Production

A synthetic peptide corresponding to the 13 C-terminal amino acids of the PmBiP deduced amino acid sequence was synthesized at the University of Victoria Protein Micro-Chemistry Centre using a Model 430A peptide synthesizer (Applied Biosystems, Foster City, Calif., USA) with the "FastMoc" chemistry software. The peptide, with an additional cysteine residue added to the N-terminal end, was then conjugated to a KLH carrier protein using the Imject™ kit and following the manufacturer's instructions (Pierce, Rockford, Ill., USA). The conjugated peptide was mixed with Freund's complete adjuvant and injected into New Zealand white rabbits. Subsequent booster injections were given at 2-week intervals using the conjugated peptide prepared in Freund's incomplete adjuvant.

7. Protein Extraction and Western Blotting

Protein extractions from whole developing seeds, mature seeds, germinating seeds, and young seedlings were performed by grinding approximately 100 mg of tissue in liquid nitrogen with a mortar and pestle. The powders were suspended individually in extraction buffer containing 65 mM Tris-HCl, pH 6.8, 1% SDS, 5% glycerol, and 2.5% β-mercaptoethanol, boiled for 5 minutes, frozen at −80° C. for 1 hour, boiled for 5 minutes, then centrifuged at 16,000×g for 25 minutes. The supernatants were collected and saved for further analysis. For subcellular fractionations (FIG. 1B), approximately 5 g of tissue were frozen in liquid nitrogen and ground to a fine powder using a mortar and pestle. The individual powders were suspended and vortexed in buffer A (100 mM Tris-HCl pH 7.5, 250 mM sucrose, 2 mM $MgCl_2$, 10 mM KCl, 1 mM phenylmethylsulfonylflouride (PMSF), and 2.8 mM β-mercaptoethanol), then filtered through two layers of Miracloth™ (Calbiochem, La Jolla, Calif., USA). The filtrates were centrifuged at 25,000×g for 30 minutes. The supernatants were collected and centrifuged at 140,000×g for 1 hour. The supernatants (soluble fractions) were saved, and the respective pellets microsomal fraction) were suspended in buffer B (50 mM phosphate buffer pH 7.5, 20% glycerol, and 10 mM β-mercaptoethanol).

Microsomes were separated into soluble and membrane fractions according to Fujiki et al., *J. Cell Biol.* 93:97–102, 1982.

To purify nuclei (nuclear fraction), the pellets from the 25,000×g centrifugation were resuspended in buffer A, layered on a 25%/75% Percoll™ (Sigma, Oakville, Ontario, Canada) step gradient, and centrifuged at 1000×g for 20 minutes. Nuclei were collected from the 25%/75% interface, washed 2× in buffer A, and suspended in buffer B.

Protein concentrations were determined by the BioRad Reagent protein assay (BioRad). Extraction and quantification of needle proteins from seasonal samples and densitometry of western blots were performed as described in Ekramoddoullah et al., *Can. J. For. Res.* 25:1137–1147, 1995. Protein samples were suspended in protein sample buffer (12.5 mM Tris-HCl pH 6.8, 2% SDS, 10% glycerol, 5% β-mercaptoethanol, and 0.1% bromophenol blue), boiled for 3 minutes, and separated by SDS-PAGE using the Mini-PROTEAN II™ gel electrophoresis system (BioRad) with a 4% (w/v) acrylamide stacking gel (80 volts; constant voltage) and an 11% (w/v) acrylamide separating gel (200 volts; constant voltage). The proteins were stained with Coomassie brilliant blue R250 or transferred to nitrocellulose membranes (Schleicher & Schuell, Keene, N.H., USA) using a Mini-Trans-Blot™ cell (BioRad) at 100 volts for 1 hour in transfer buffer (25 mM Tris, 190 mM glycine, 20% methanol, and 0.1% SDS). The membranes were blocked overnight at 4° C. in Tris-buffered saline ("TBS"; 20 mM Tris, 500 mM NaCl; pH 7.5) containing 0.05% Tween-20 ("TTBS"), incubated with primary antibody (diluted 1:3000 in TTBS) for 90 minutes at room temperature, then washed two times with TTBS (5 minutes each). The membranes were then incubated with an alkaline phosphataseconjugated goat anti-rabbit antibody (1:3000 dilution in TTBS) (Cedar Lane Laboratories Ltd., Hornby, Ontario, Canada) for 45 minutes at room temperature, followed by washing in TTBS (5 minutes) and TBS (5 minutes). Immunoreactive bands were visualized by incubating the membrane with 5-bromo- 4-chloro-3-indolyl-phosphate (0.165 mg/ml) and nitroblue tetrazolium (0.33 mg/ml) as substrate in buffer containing 100 mM NaHCO$_3$ pH 9.8 and 1 mM MgCl$_2$.

C. Expression Pattern of PmBiP mRNA and Protein

To understand better the developmental regulation of PmBiP, the pattern of PmBiP mRNA and protein expression during seed and seedling development was examined using northern and western blotting. Western blotting also was used to determine whether seasonal variations exist in PmBiP protein levels in the needles of one-year-old seedlings.

Both before and soon after fertilization (FIG. 1; May 31 and June 19, respectively), the amount of PmBiP mRNA observed in developing seeds was approximately 50- to 100-fold higher than the amount observed during embryogenesis (FIG. 1; July 12–August 15). During embryogenesis, northern blotting of dissected material showed similar amounts of PmBiP mRNA in both the megagametophyte and developing embryo. Western blot analysis of seeds collected at various stages of seed development showed that the amount of PmBiP protein also was high before and soon after fertilization, and decreased thereafter.

Figure 2:
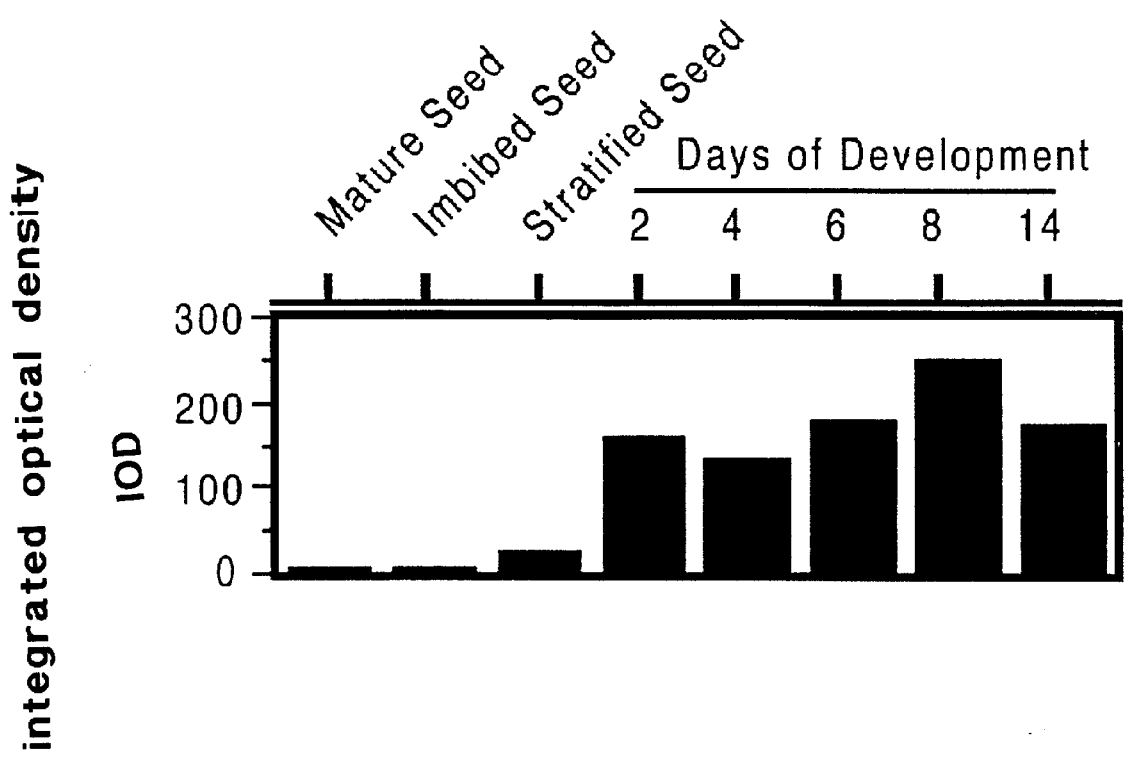
FIG. 2 is a graph depicting the expression of PmBiP RNA during germination and early seedling development. Total RNA was isolated from tissue collected at the indicated time points and subjected to northern blot analysis (20 μg per lane) using the PmBiP cDNA as probe. The same membrane was stripped and re-probed with a genomic DNA probe encoding the Douglas-fir 18S rRNA subunit to account for differences in the amount of RNA loaded per lane. Differences in the amount of PmBiP transcript were adjusted for differences in the amount of RNA loaded per lane (given in units of integrated optical density).

Following imbibition and stratification, PmBiP mRNA increased slightly (FIG. 2). Upon exposure of the seeds to germination conditions, the amount of PmBiP mRNA increased to levels greater than the level observed during early stages of seed development. Levels increased 150- to 200-fold over levels observed in mature or imbibed seeds after only a 2-day exposure to germination conditions. PmBiP mRNA amounts were highest after 8 days, approximately 250-fold higher than observed in mature seeds. The amount of PmBiP protein did not show an increase until 8 days after exposure of the stratified seeds to germination conditions, with the highest amounts appearing after 14 days.

Figure 3:
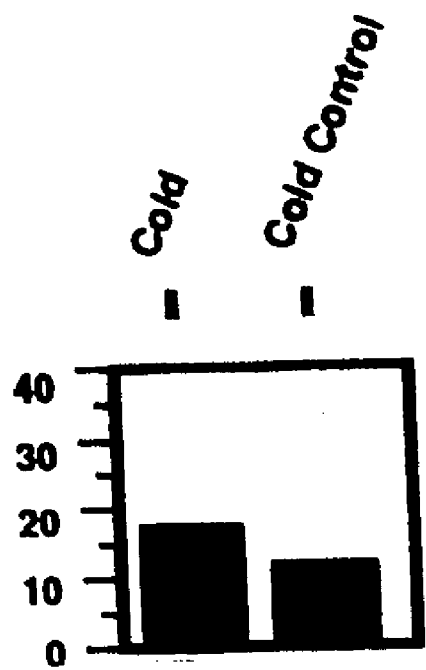
FIG. 3 is a graph showing changes in PmBiP RNA levels in response to cold treatment. The RNA was isolated from 14-day-old seedlings and analyzed by northern blot procedures.

Temperature regulation of PmBiP protein expression was observed at both the mRNA level and the protein level. 14-day-old seedlings were subjected to cold treatment, and mRNA and protein levels were assessed. After the cold treatment both protein levels and mRNA levels (FIG. 3) were found to be increased.

Figure 4:
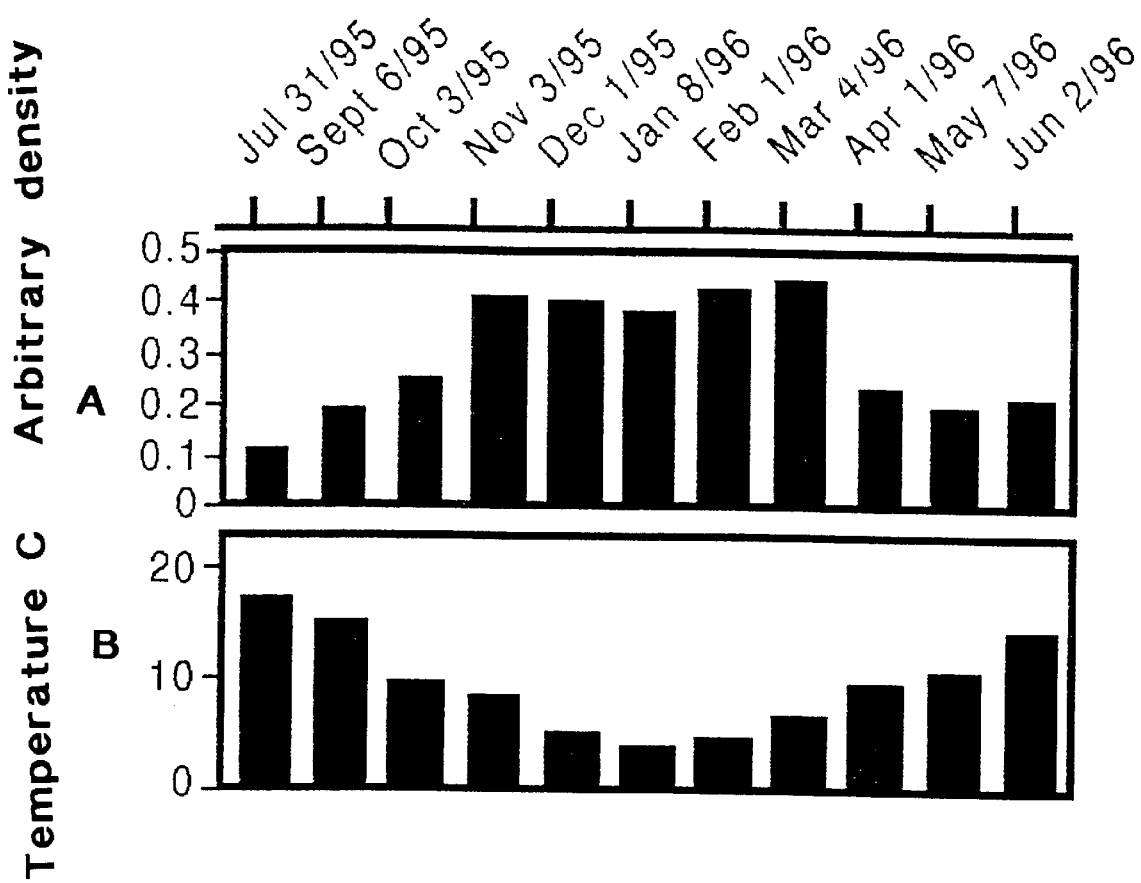
FIG. 4 is a graph showing the seasonal variation of PmBiP protein in needles from 1-year-old seedlings. Total protein was isolated from the needles of 1-year-old Douglas-fir seedlings at the indicated times and subjected to western blot analysis (15 ∞g per lane). Following blot development, immunoreactive bands were quantified using scanning densitometry and displayed graphically (given in units of arbitrary density). (A) shows PmBiP protein levels, and (B) shows the monthly average temperatures (given in degrees Celsius) to allow direct comparison at each time point.

In an additional set of experiments, the abundance of PmBiP protein was, followed over a one-year period in needles collected from 1-year-old Douglas-fir seedlings kept under natural day-length and temperature in an outdoor shelter house FIG. 4). PmBiP protein levels showed seasonal variation, with the highest mounts occurring in needles taken from seedlings during the winter when the monthly average temperature was below 10° C.

D. Materials and Methods Relating to the Characterization of the PmBiP Promoter

1. Plant Material

Tobacco plants (Xanthi) and 4–6 week old potato plants (Desiree) for use in transformation were grown in Majenta jars on hormone free MS medium (Murashige and Skoog, *Physiol. Plant* 115:473–497, 1962 under a 16 hours light/8 hours dark photoperiod at a constant temperature of 23° C.

Growth of Arabidopsis plants used for transformation was as follows: Approximately 10–20 *Arabidopsis thaliana* (L.) Heynh. seeds of ecotype Columbia were placed on a nylon screen covering moistened Sunshine™ mix #3 soil (Sun Gro Horticulture, Bellevue, Wash., USA) on 10-cm-diameter pots, and then covered with Saran Wrap™ secured with an elastic band. Pots were then placed at 4° C. for 2 days to promote uniform germination. Pots were placed in a growth chamber with an 18 hours 24° C. day/6 hours 22° C. night cycle with 150 $\mu Em^{-2}s^{-1}$ of light. The Saran Wrap™ was removed when plants began to push against its surface (approximately 2 days).

Growth of Douglas-fir embryos used for transient expression was as follows: Interior Douglas-fir (*Pseudolsuga menziesii* [Mirb.] Franco) seeds (seed-lot 8912) were imbibed for 2 days at 4° C., then surface-sterilized in 50% industrial bleach (6% sodium hypochlorite) for 20 minutes at room temperature. Embryos were aseptically dissected from seeds and placed on woody plant medium (WPM; Table 1; Lloyd and McCown, *Proc. Int. Plant Prop. Soc.* 30:421–427, 1980) at 22° C. in the dark for 16 hours before particle bombardment.

2. Inverse PCR and Cloning

Inverse PCR was conducted based on the method described in Ochman et al. et al., *Amplification of Flanking Sequences by Inverse PCR,* 1980, and Innis et al. (eds.) *PCR Protocols; A Guide to Methods and Applications,* Academic Press Inc., San Diego, 1990, as follows. Douglas-fir genomic DNA was extracted from spring-flush needles by a modification of the CTAB method of De Verno et at., *Constructing Conifer Genomic Libraries; A Basic Guide,* Petawawa National Forestry Institute, Canadian Forest Service, 1989. Approximately 18 $\mu$g of DNA was digested with XbaI or SacI overnight at 37° C. Each reaction was heat-inactivated at 65° C. for 20 minutes, then suspended in 10 ml of ligation buffer (50 mM Tris-HCl pH 7.4, 10 mM MgCl$_2$, 10 mM dithiothreitol, and 1 mM ATP) with 0.02 Weiss units/$\mu$L T4 DNA ligase for 16 hours at 15° C. Circularized DNA was precipitated by the addition of 1/10 volume of 2.5 M ammonium acetate, followed by 2 volumes of −20° C. 100% ethanol on ice, then centrifuged at 25,000×g for 10 minutes at 4° C. Precipitated DNA was suspended in 60 $\mu$L of sterile distilled H$_2$O of which 5 $\mu$L was subjected to PCR using Taq PCR MasterMix™ (QIAGEN, Mississauga, Ontario, Canada) and 250 pmol of the following primers in a 100-$\mu$L reaction: XbaI used primer combinations p5-3z8 (5'-AAT GAA AGC GAA GTG ACA CC-3'; SEQ ID No: 19) and p14-5a4 (5'-CAG AAC CAT TAA CAA GAG CAA GAT 3'; SEQ ID NO: 20) or p14-5z1.1 (5'-AAC CAG CAG TGA TAA ACG CC-3'; SEQ ID NO: 21) and p14-5a4; SacI used primer combinations p5-3z8 and p14-5a3 (5'-TAT GGT TTG GAT AAA AAG GGA G-3'; SEQ ID NO: 22) or p14 5z1.1 and 14-5a3. Conditions for PCR consisted of 1 cycle of denaturing at 95° C. for 5 minutes and 1 minute at 75° C., 30 cycles of denaturing at 94° C. for 1 minute, primer annealing at 56° C. for 1 minute and an extension of 72° C. for 2 minutes, followed by a final elongation step at 72° C. for 5 minutes. Aliquots of each reaction (20 $\mu$L) were separated on an agarose gel and subjected to Southern blotting to identify potential promoter fragments. PCR reactions containing positive fragments were cloned into the pCR®2.1-TOPO vector using the TOPO TA™ Cloning Kit (Invitrogen, Carlsbad, Calif., U.S.A.) according to the manufacturer's instructions. Colonies containing an appropriately sized insert were screened using PCR with the appropriate primers followed by Southern blotting. Plasmid DNA for colony screening using PCR was obtained by suspending colonies in 200 $\mu$L of distilled H$_2$O, followed by incubation at 85° C. for 5 minutes. Samples were centrifuged at 16,000×g for 5 minutes, and 36 $\mu$L were removed and used as a template for PCR.

3. DNA Sequencing

PmBiP promoter (SEQ ID NO: 31) and expression constructs were sequenced using the Big Dye™ Superscript Terminator Cycle sequencing Ready Reaction (Perkin Elmer) and oligo primers with the ABI Prism automated 377 DNA Sequencer (Perkin Elmer). Plasmid DNA for sequencing was isolated using the Wizard™ 373 DNA Purification System (Promega, Madison, Wis., U.S.A.). DNA sequence trace files were assembled using the DNASTAR™ program SeqMan (DNASTAR Inc, Madison, Wis., U.S.A.).

4. Sequence Analysis

Analysis of the PmBiPPro1 DNA sequence and identification of putative regulatory elements were performed done by searching the plant cis-acting DNA regulatory database (PLACE; Higo et al., *Nucl. Acids Res.* 27:297–300, 1999).

5. Southern Blotting

DNA was electrophoresed on a 1% agarose gel and transferred to a Zeta Probe™ membrane (BioRad, Mississauga, Ontario, Canada) according to the manufacturer's instructions. The PmBiP3 cDNA was $^{32}$P-labelled with a random-primers DNA labeling kit (GIBCO BRL, Burlington, Ontario, Canada). Hybridization and washing were performed according to the standard protocol in the Zeta Probe manufacturer's instructions. Blots were exposed using Kodak X-OMAT AR film (Eastman Kodak Company, Rochester, N.Y., U.S.A.) overnight at −80° C.

6. Construction of Vectors Containing PmBiP Promoter Sequences

The following promoter-gene fusions were constructed for expression in the cytosol: Plasmids were constructed from parent plasmids pBI121 and pBI221 for stable and transient expressions, respectively. PmBiP promoter constructs were generated using PCR with either Taq polymerase (PmBiPpro1-1; Quiagen) or DeepVent™ polymerase (PmBippro1-3 and PmBiPpro1 5; NEB) and the PmBiPpro1 clone as template. The primers, containing HindIII and XbaI sites (bold), used for amplification of the various promoter constructs, employed the same 3'-primer (5'-TCG AAG CGC AAA TCT AGA GTT TAA ACT TCC-3'; SEQ ID NO: 23) and the following 5'-primers: PmBiPPro1-1 (5'-AAG AAG GCA AGC TTT CAA CTA A-3'; SEQ ID NO: 24), PmBiPPro1-3 (5'-GCA TAA GAA AGC TTC TAC CCT G-3'; SEQ ID NO: 25), and PmBiPPro1-5 (5'-GCA CTA GGA AGC TTG GGA ACT C-3'; SEQ ID NO: 26). Following restriction digestion, the resulting products (PmBiPpro1-1, 2263 bp, SEQ ID NO:16; PmBiPpro1-3, 1259 bp, SEQ ID NO: 17; PmBiPpro1-5, 263 bp, SEQ ID NO: 18) were cloned into the HindIII and XbaI sites of pBI221, replacing the CaMV 35S promoter (~0.8 kb). The resulting plasmids, containing PmBiP promoter sequences, were labeled pPRO1-1221, pPRO1-3221, and pPRO1-5221. Replacing the HindIII-XbaI fragment in pBI121 (containing the CaMV 35S promoter) by HindIII-XbaI fragments from pPRO1-1221, pPRO1-3221, and pPRO1-5221 respectively, created the plasmids pPRO1-1121, pPRO1-3121, and pPRO1-5121.

7. Transient Expression

Germinated Douglas-fir zygotic embryos were bombarded using the model PDS-1000/He Biolistic® Particle Delivery System (BioRad). DNA (pBI221 plasmid derivatives) was coated onto gold particles (1–3 μm diameter; Sigma-Aldrich Canada Ltd, Oakville, Ontario, Canada) as described by Jefferson, *Plant Mol. Biol. Rep.* 5:387–405, 1987, as follows. A gold suspension (60 mg/ml) was prepared in 50% glycerol of which 15 μL was placed in 1.5-ml microfuge tubes with $4.2 \times 10^{11}$ copies of either a CaMV 35S:GUS plasmid (pBI221, 5700 bp; Clontech Laboratories Inc, Palo Alto, Calif., U.S.A.), a plasmid containing PmBiPpro1-1 (SEQ ID NO: 16) (7188 bp), a plasmid containing PmBiPpro1-3 (SEQ ID NO: 17) (6184 bp), or a plasmid containing PmBiPpro1-5 (SEQ ID NO: 18) (5189 bp), 15 μL of 2.5 M $CaCl_2$, and 6 μL of 0.1 M spermidine with continuous vortexing. The particles were allowed to settle on ice, then pelleted by a brief centrifugation. The supernatant was discarded, and 70 μL cold 70% ethanol was added without disturbing the pellet. The 70% ethanol was then removed, and an additional 70 μL cold 100% ethanol was added without disturbing the pellet. This too was removed and the particles suspended in 30 μL cold 100% ethanol with slow vortexing. Aliquots of 10 μL were placed on a macrocarrier disk and allowed to dry in the presence of silica gel desiccant. Each bombardment delivered $1.4 \times 10^{11}$ constructs and was conducted using the following parameters. The gap distance between the rupture disk and macrocarrier was 0.6 cm, the macrocarrier travel distance was 0.6 cm, the target tissue distance was 8 cm from the microcarrier launch assembly platform, the sample chamber vacuum was 25 inches of mercury, and rupture pressure was 1550 psi. Tissue then was incubated on WPM at 22° C. in the dark for 48 hours prior to histochemical GUS staining. Following GUS staining (see below), the number of blue spots were counted under a stereo dissecting microscope.

8. Arabidopsis Transformation

*Arabidopsis thaliana* plants were transformed according to the method of Clough and Bent, *Plant J.* 16: 735–743, 1998. *Agrobacterium tumefaciens* strain MP90 carrying the plasmid CaMV 35S:GUS or PmBiPPro1 (SEQ ID NO:16): GUS was grown to stationary phase in liquid culture at 28° C., 250 rpm, in sterile LB broth (10 g tryptone, 5 g yeast extract, 5 g NaCl per liter of water) containing 50 μg/ml kanamycin and 10 μg/ml gentamycin. Cells were harvested by centrifugation for 20 minutes at room temperature at 5500×g, then suspended in infiltration medium (5.0% sucrose and 0.05% Silwet L-77 (Lehle Seeds, Round Rock, Tex., U.S.A.)) to a final $OD_{600}$ of approximately 0.8 prior to use. The above-ground portions of plants were dipped in infiltration medium containing Agrobacterium for 3–5 sec with gentle swirling 2 days after removal of the primary bolt. One subsequent dip was made 7 days later. Following each dip, the plants were covered with a plastic bag for 24 hours to retain moisture. Plants were grown normally and fed with HI•SOL™ 18-24-12 soluble plant food (1 g/L; Green Valley Fertilizer, Abbotsford, B.C, Canada) once a week via sub-irrigation. Plants were no longer watered after seed pods began to turn brown. When plants were fully dried, they were placed in a brown paper bag for 1 week prior to collecting seed. Seeds were collected by manually rubbing plants and pods, then filtering the debris through a 0.707-mm mesh sieve (W.S. Tyler Company of Canada Ltd., St. Catherines, Ont., Canada) several times until the seeds were reasonably free of other matter.

Seeds were sterilized using vapor-phase sterilization as follows (Clough and Bent, *Plant J.* 16:735–743, 1998). Collected seeds were placed in 15-ml conical tubes (2–3 ml seeds per tube) with lids attached loosely. Tubes were placed in a rack inside a plastic vacuum dessicator (Bel-Art #42025, 240-mm internal diameter) containing a 250-ml glass beaker with 150 ml bleach (5.25% sodium hypochlorite). Five ml of concentrated HCl were placed in a 10-ml glass beaker and floated on top of the bleach solution. The lid was placed on the dessicator and a slight vacuum applied. The dessicator was shaken slightly to spill the concentrated HCl into the bleach to liberate chlorine gas for overnight sterilization. Sterile seeds were sprinkled on 150×15 mm² selection plates (½ MS media/0.8% agar/1% sucrose, 50 μg/ml kanamycin, 100 μg/ml ampicillin) and placed in dark at 4° C. for 2 days. Plates were removed and placed in a growth chamber with 16 hours/8-hours light/dark at 22° C. for 2 weeks. Healthy green transformants were selected and placed in moist soil in a growth chamber with an 18-hour 24° C. day/6-hour 22° C. night cycle with 150 μEm$^{-2}$s$^{-1}$ of light. The plants were covered with Saran Wrap™ for the first 2 days.

9. Tobacco and Potato Transformation

Leaf strips from tobacco and stem segments (5–10 mm pieces) and leaves 20 (cut at the base) from potato were pre-cultured upside down for 3–5 days on MS 104 medium (MS medium supplemented with 1 μg/ml BAP, 0.1 μg/ml NAA, pH=5.7). Explants were incubated in S2 medium (MS medium without agar but supplemented with 0.5 g/L MES and 20 g/L mannitol) inoculated with a 1:200 (v:v) dilution of an overnight culture of *Agrobacterium tumefaciens* strain MP90 for 2–3 days under low light intensity. An overnight culture of *Agrobacterium tumefaciens* was grown at 28° C. in LB media supplemented with 50 μg/ml kanamycin and 10 μg/ml gentamycin. Explants were incubated at low light intensity on Stage I medium (MS medium supplemented with 6 g/L agarose (instead of 8 g/L agar), 200 mg/L glutamine, 600 mg/L MES, 500 mg/L PVP, 20 g/L mannitol, 20 g/L glucose, 40 mg/L adenine-SO$_4$, 2.5 mg/L zeatine-riboside, 0.1 mg/L NAA, and 0.02 mg/L GA$_3$) for 3–5 days followed by transfer to Stage II medium (Stage I medium supplemented with 100 μg/ml kanamycin and 500 μg/ml cefotaxime) for 7–12 days to initiate growth of callus. To initiate growth of shoots, explants containing callus were transferred to stage III medium (Stage II medium containing no NAA) for 5–7 weeks. Following shoot formation, plantlets were transferred to rooting medium (MS medium supplemented with 50 μg/ml kanamycin and 250 μg/ml cefotaxim) and grown as described for parent plants.

10. Histochemical GUS Staining

GUS staining was performed based on the method described by Jefferson, *Plant Mol. Biol. Rep.* 5:387–405, 1987. Tissue from particle bombardment or transgenic plants was immersed in solution containing 1 mM X-Gluc, 100 mM sodium phosphate buffer pH 7.0, 10 mM EDTA, 0.5 mM potassium ferricyanide, 0.5 mM potassium ferrocyanide, 0.1% triton X-100, and incubated overnight at 37° C.

11. In vitro GUS assay

Fresh plant tissue was placed in a 1.5-ml Eppendorf tube containing ice-cold lysis buffer (50 mM sodium phosphate pH 7.0, 10 mM EDTA, 0. 1% Triton X-100, 0.1% sarkosyl, 10 mM β-mercaptoethanol, and 0.02 g/ml insoluble polyvinylpyrrolidone (PVP)), and homogenized using a glass pestle connected to a Bamant series 10 mixer (Barnant Company, Barrington, Ill., USA). Homogenates were centrifuged at 16,000×g for 15 minutes at 4° C. Supernatants were collected and assayed for protein using the method of Bradford, *Anal. Biochem.* 72:248–254, 1976. GUS activity was measured in 100 μL extraction buffer (without PVP) containing 6 μg of total protein and 1 mM p-nitrophenyl-β-D-glucuronide as substrate at 37° C. using a Thermomax™ microplate reader and Softmax™ Pro v3.1 software (Molecular Dynamics Corporation). Absorbance was measured at 405 nm every 5 minutes or after 18 hours.

D. Expression Pattern of GUS Transgene Under the Control of PmBiP Constructs

Results from sequencing the PmBiP promoter (SEQ ID NO: 31) revealed that it contains several possible cis-acting elements (FIG. 5). Furthermore, several of the identified cis-acting elements are believed to be responsible for promoter activity in response to environmental changes (i.e., inducible), such as light, temperature, wounding, and water stress. Other identified promoter elements indicate that the endogenous PmBiP promoter (SEQ ID NO: 31) contains negative regulatory regions. One of skill in the art will appreciate that the identification of these regions, and the other elements shown in FIG. 6, facilitates the subsequent modification of the PmBiP promoter (SEQ ID NO: 31). Thus, the PmBiP promoter (SEQ ID NO: 31) can be modified via deletion of negative regulatory elements to increase transcription, or to alter the induciblity of the promoter via the addition or deletion of inducible elements.

Figure 6:
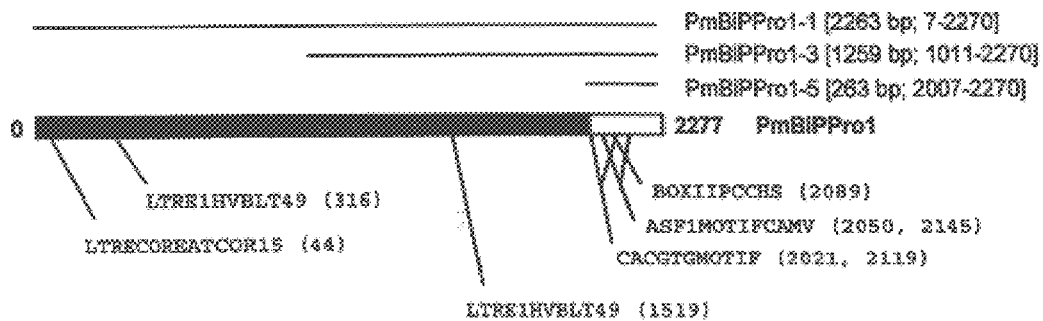
FIG. 6 is a schematic diagram showing a comparison of the full-length PmBiPPro1 sequence (SEQ ID NO: 31; PmBiPPro1) to the deletion constructs PmBiPPro1-1 (SEQ ID NO: 16), PmBiPPro1-3 (SEQ ID NO: 17), and PmBiPPro1-5 (SEQ ID NO: 18).

The isolation and sequencing of the PmBiP promoter (SEQ ID NO: 31) also facilitated the creation of the deletion constructs PmBiPPro1-1, PmBiPPro1-3, and PmBiPPro1-5 (FIG. 6). These deletion constructs were used to stably transform Arabidopsis, potato, and tobacco, as well as to transiently transform Douglas-fir zygotic embryos.

Figure 7:
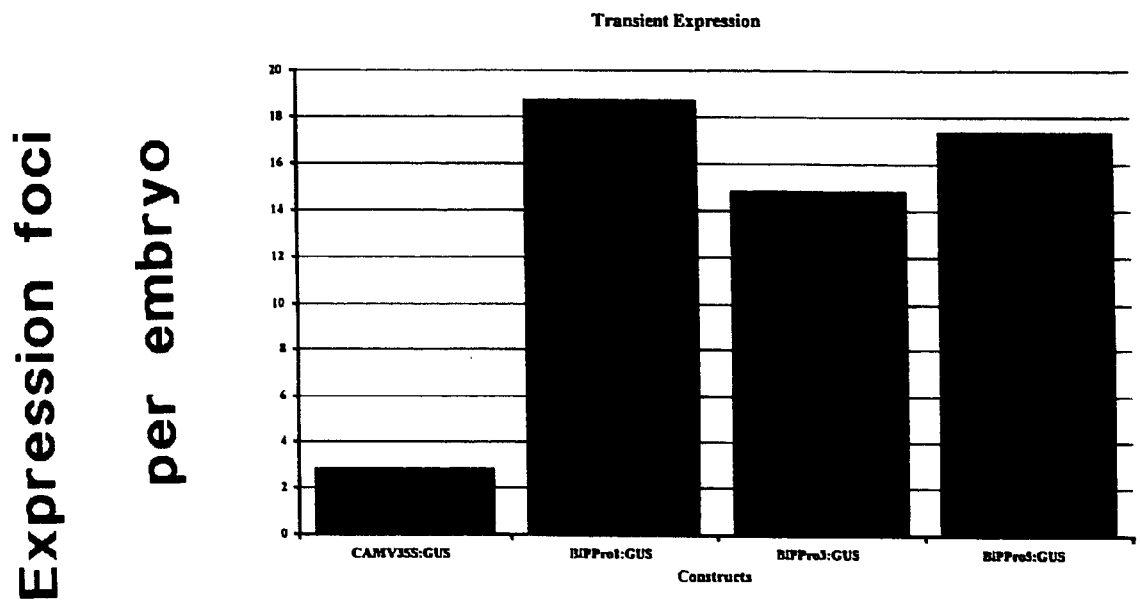
FIG. 7 is a graph of the results from the transient expression of GUS in Douglas-fir zygotic embyros under the control of the CaMV35S, PmBiPPro1-1 (SEQ ID NO: 16), PmBiPPro1-3 (SEQ ID NO: 17), and PmBiPPro1-5 (SEQ ID NO: 18) promoter sequences. The results represent the average of two trials, each trial involving ten embryos, and the data is reported as an average number of expression foci per embyro.

Douglas-fir zygotic embryos were transiently transformed with construct containing the GUS open reading frame under the control of PmBiPpro1-1, PmBiPpro1-3, PmBiPpro1-5, or CaMV35S. The results (FIG. 7) showed that all of the PmBiP promoter constructs were capable driving the expression of GUS. Additionally, even the relatively weak PmBiP promoter construct (PmBiPpro1-3) was capable of driving expression of the transgene at a rate 7-fold higher than the rate exhibited by the control CaMV35S promoter construct (average expression levels taken over two trials, ten embyros per trial).

Potato and tobacco plantlets that were stably transformed with either the GUS open reading frame under the control of PmBiPpro1-1, PmBiPpro 1-3, PmBiPpro1-5, or CaMV35S showed that even PmBiPpro1-5, the smallest deletion, was capable of driving the expression of GUS. Moreover, the PmBiPpro1-5 construct showed promoter activity that was comparable to the activity of the control CaMV35S construct.

Figure 8:
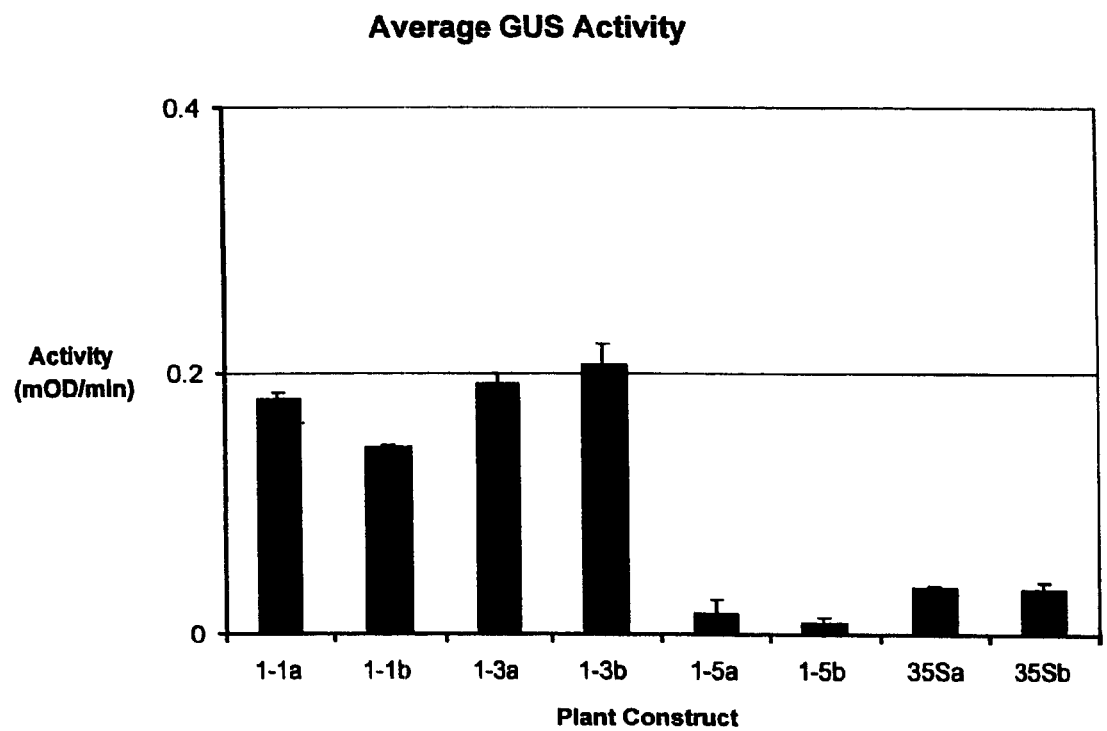
FIG. 8 is a graph of data from in vitro GUS activity of 19-day-old transgenic Arabidopsis plants containing various PmBiPPro1 constructs. GUS activity was measured in 6 μg of total protein extracted from whole seedlings as described herein. Two transformants were examined for each construct. Results represent the average and standard deviation of three trials for each plant extract.

Stably transformed 19-day-old Arabidopsis plants also were tested for GUS expression levels. The results showed that the highest level of GUS expression was in plants transformed with the PmBiPpro1-3 construct. However, plants transformed with PmBiPpro1-1 showed very similar levels of expression (FIG. 8).

Figure 9:
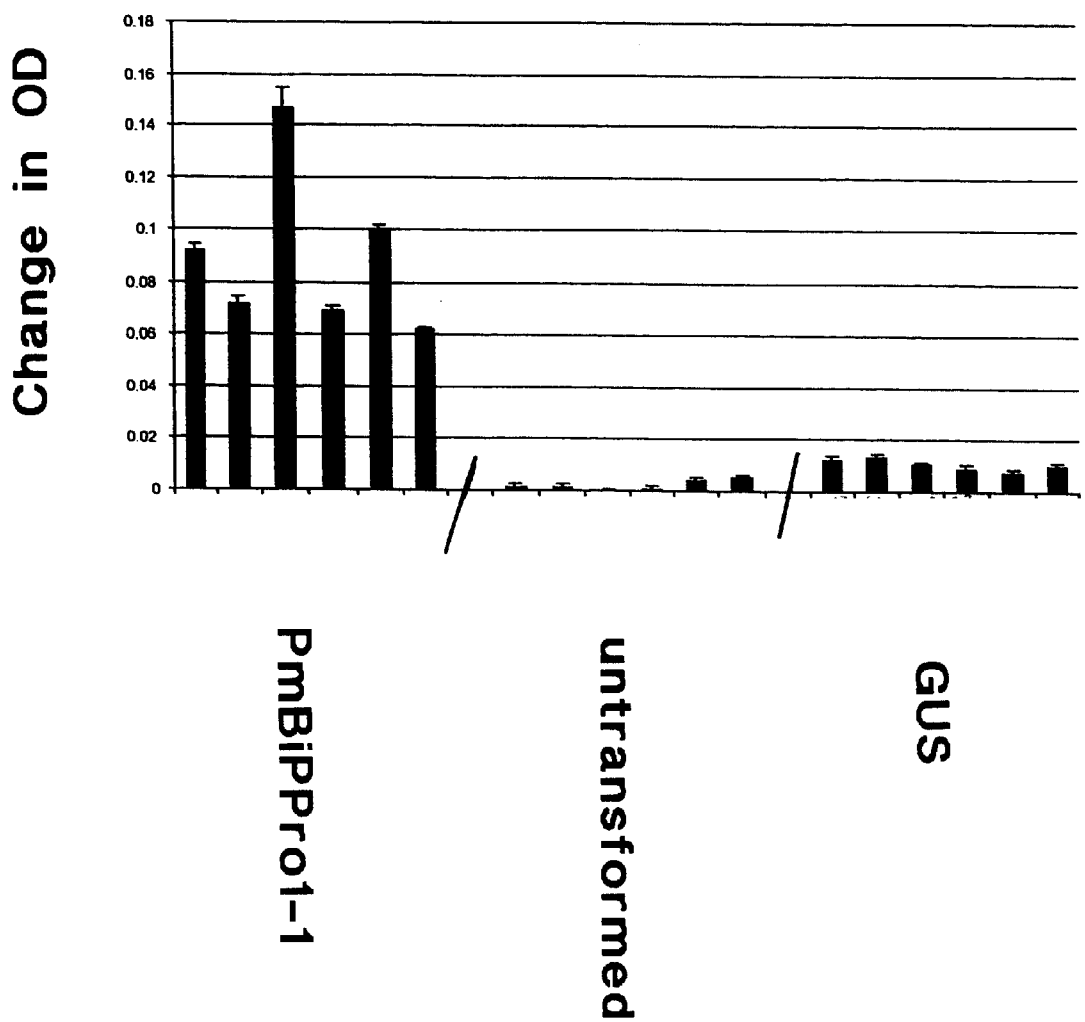
FIG. 9 is a graph of the results from PmBiPPro1-1 (SEQ ID NO: 16) expression in response to wounding in 21-day-old Arabidopsis cotyledons. One cotyledon was wounded from each plant, while the other served as control. GUS activity was measured in 6 μg of total protein extracted, 18 hours after wounding (pinching with forceps). GUS activity is measured as change in absorbance (ΔOD) after 18 hours. GUS assays also were performed on wounded untransformed and CaMV35S:GUS plant cotyledons. Results represent the average and standard deviation of three trials for each plant extract induced via wounding.

The ability of the PmBiP promoter to be induced via wounding was tested in stably tranformed 21-day-old Arabidopsis cotyledons (FIG. 9). One cotyledon was wounded by pinching with forceps, and the second cotyledon was used as a control. The results showed that the PmBiPpro1-1 (SEQ ID NO: 16) construct is wound-inducible. This data, coupled with the PmBiP protein expression data described above, showed that the PmBiP promoter (SEQ ID NO: 31) is inducible at least by wounding and upregulated by temperature alterations. These attributes make this promoter particularly useful in situations where it is desirable to produce a protein at cold temperatures (i.e., where increased protein stability is desired). "Cold" implies that the plant is being grown at a colder temperature than otherwise would be optimal for host growth. For example, a plant or a plant part (i.e., a leaf, or stem) can be wounded and placed in a cold temperature, such as at less than 20° C., less than 15° C., or less than 10° C. Additionally, the table of cis-acting elements provided in FIG. 5 shows that it is likely that the PmBiP promoter (SEQ ID NO: 31) is inducible by many other environmental factors.

V. Alteration of Promoter Structure

A. Modifications of the Douglas-fir Luminal Binding Protein (PmBiP) Promoter The structure of a given promoter determines the level of mRNA expression as well as specificity of the promoter. However, expression levels and/or specificity can be maintained when deletions, substitutions, and/or additions are made to the promoter sequence. Hence, the scope of the invention encompasses PmBiP promoters that have been modified through the incorporation of deletions, substitutions, and/or additions. However, regardless of the number of mutations that are incorporated into the PmBiP promoter (SEQ ID NO: 31), the promoter continues to exhibit promoter activity, or native PmBiP promoter activity, as described above.

One possible method of modifying the PmBiP promoter (SEQ ID NO: 31) is by inserting additional promoter elements into the promoter sequence. For example, the promoter can be modified such that an E-box motif, RY-repeated element, AT-rich region, ACGT-core element, opaque-2-like binding site, and/or a conserved gymnosperm-like region is added. One of skill in the art will appreciate that standard molecular biology techniques can be used to insert one or more of these elements into the promoter sequence. The modified promoter then can be transiently transfected into gymnosperm, monocot, or dicot tissue and the tissue can be tested for transgene expression.

Similarly, one or more of the existing promoter elements can be deleted from the promoter sequence. The modified promoter can be tested for transcriptional activity and specificity. Given the disclosure of the PmBiP promoter (SEQ ID NO: 31) and the above-described materials and methods, it also is possible to make both additions and deletions and test for promoter activity.

Finally, the PmBiP promoter (SEQ ID NO: 31) also can be modified such that the inter-element spaces contain deletions, insertions, and/or substitutions. One of ordinary skill in the art can use standard molecular biology techniques to insert additional nucleic acid residues into the inter-element spaces, delete nucleic acid residues from the inter-element spaces, and/or substitute other sequences into the inter-element spaces. However, regardless of the number and combination of insertions, deletions, and substitutions, the PmBiP promoter (SEQ ID NO: 31) will maintain promoter activity. In some cases, the promoter will maintain native PmBiP promoter activity.

B. Methods for Producing the Douglas-fir PmBiP Promoter, and Variants and Deletion Mutants Thereof

1. Cloning Nucleic Acid Sequences Encoding PmBiP

Provided with the nucleic acid sequence of the Douglas-fir PmBiP promoter (SEQ ID NO: 31), one of ordinary skill in the art will appreciate that several different methods can be used to isolate the Douglas-fir PmBiP promoter (SEQ ID NO: 31). One example of such a method is the polymerase chain reaction (PCR) (U.S. Pat. No. 4,683,202 to Mullis; and Saiki et al., *Science* 239:487–491, 1988). After isolation, the PmBiP promoter (SEQ ID NO: 31) sequence is useful for driving the expression of transgenes.

When using PCR to isolate a sequence encoding a gene, a first primer can be designed that targets the extreme 5'-end of the sequence, and a second primer can be designed that targets the extreme 3'-end of the sequence. These primers can be used to generate multiple copies of the promoter sequence. The copies are isolated by separation on an agarose gel. The fragment of interest is then removed from the gel and ligated into an appropriate vector.

Alternatively, a promoter can be created by engineering synthetic strands of DNA that partially overlap each other (Beaucage and Caruthers, *Tetrahedron Letters* 22:1859–1869, 1981; and Matthes et al., *EMBO J.* 3:801–805, 1984). The synthetic strands are annealed, and a DNA polymerase is used to fill in the single-stranded regions. The resulting synthetic double-stranded DNA molecule can be cloned into a vector.

For use as primers and probes, nucleic acid sequences can contain at least 15 contiguous nucleic acid molecules of the sequences shown in SEQ ID NOS: 16, 17, 18, and 31, or the complementary strand of the molecule shown in SEQ ID NO: 31. The nucleic acid sequences are useful for performing hybridization protocols, such as northern blots or Southern blots as described in Sambrook et al. (eds.). *Molecular Cloning, A Laboratory Manual,* 2d ed., vol. 1-3, Cold Spring Harbor Laboratory Press, Cold Spring Harbor, N.Y., 1989.

These hybridization protocols can be used to identify nucleic acid sequences that are substantially similar to the sequences shown in SEQ ID NOS: 16, 17, 18, and 31. A successful hybridization to such sequences indicates that the analogous nucleic acid sequence hybridizes to the oligonucleotide probe that comprises at least a fragment of the sequences shown in SEQ ID NOS: 16, 17, 18, and 31. Generally, hybridization conditions are classified into categories, for example very high stringency, high stringency, and low stringency. The conditions corresponding to these categories for probes of approximately 600 bp are provided below.

| Very High Stringency (detects sequences that share 90% sequence identity) | | | | |
|---|---|---|---|---|
| Hybridization | in | 5x SSC at | 65° C. | 16 hours |
| Wash twice | in | 2x SSC at | room temp. | 15 minutes each |
| Wash twice | in | 0.2x SSC at | 65° C. | 20 minutes each |
| High Stringency (detects sequences that share 80% sequence identity or greater) | | | | |
| Hybridization | in | 3x SSC at | 65° C. | 16 hours |
| Wash twice | in | 2x SSC at | room temp. | 15 minutes each |
| Wash twice | in | 0.5x SSC at | 55° C. | 20 minutes each |
| Low Stringency (detects sequences that share greater than 50% sequence identity) | | | | |
| Hybridization | in | 3x SSC at | 65° C. | 16 hours |
| Wash twice | in | 2x SSC at | room temp. | 20 minutes each |

Variant PmBiP promoter (SEQ ID NO: 31) sequences may be produced by standard DNA-mutagenesis techniques, for example, M13 primer mutagenesis. Details of these techniques are provided in Sambrook et al. (eds.), *Molecular Cloning: A Laboratory Manual,* 2nd ed., vol. 1-3, Ch. 15, Cold Spring Harbor Laboratory Press, Cold Spring Harbor, N.Y., 1989; and Ausubel et al. (eds.) *Current Protocols in Molecular Biology,* Greene Publishing and Wiley-Interscience, New York (with periodic updates), 1987. By the use of such techniques, variants can be created that differ slightly from the PmBiP promoter sequences specifically disclosed, yet that still encode a promoter having promoter activity. DNA molecules and nucleotide sequences that are derivatives of those specifically disclosed herein and that differ from those disclosed by the deletion, addition, or substitution of nucleotides while still maintaining promoter activity and/or native PmBiP promoter activity are comprehended by this invention.

2. Transformation

The DNA constructs of the invention, containing the PmBiP promoter (SEQ ID NO: 31) operably linked to one or more transgenes may be either homologous or heterologous to the host in question. If homologous to the host cell, i.e., if the transgene is produced by the host cell in nature, then the construct may be connected operably to a different secretory signal sequence and/or terminator sequence than in the natural environment. In this context, the term "homologous" is intended to include a cDNA sequence encoding a transgene that is native to the host cell. The term "heterologous" is intended to include a transgene not expressed by the host cell in nature. Thus, the DNA sequence may be from another organism, or it may be a synthetic sequence.

The host cell of the invention, into which the DNA construct or the recombinant expression vector of the invention is to be introduced, may be any cell capable of driving expression of the PmBiP promoter (SEQ ID NO: 31). Such cells include bacteria cells, yeast cells, fungal cells, insect cells, plant cells, and other higher eukaryotic cells.

Various methods of introducing the DNA construct into host cells are well known in the art. For example, in some species, the Ti plasmid of *A. tumefaciens* can be used to transform host cells (Gouka et al., *Nature Biotech.* 6:598–602, 1999). The host cell also can be transformed using gene blasting techniques (described above) and standard chemical treatments.

Having illustrated and described the principles of the invention in multiple embodiments and examples, it should be apparent to those skilled in the art that the invention can be modified in arrangement and detail without departing from such principles. Therefore, the invention includes all modifications coming within the spirit and scope of the following claims.

What is claimed is:

1. A recombinant promoter, capable of driving expression of an open reading frame (ORF) operably linked to the promoter, wherein the promoter comprises a nucleic acid sequence that shares at least 90% sequence identity to SEQ ID NO: 18.

2. A vector, comprising the promoter of claim 1.

3. A host cell, comprising the vector of claim 2.

4. A transgenic plant, comprising the host cell of claim 3.

5. A transgene, comprising the promoter of claim 1 and at least one ORF operably linked to the promoter.

6. The transgene of claim 5, wherein the ORF encodes a cationic peptide.

7. A vector, comprising the transgene of claim 5.

8. A plant cell, comprising the vector of claim 7.

9. The plant cell of claim 8, wherein the plant cell is obtained from a plant selected from the group consisting of: maize, wheat, nice, millet, tobacco, sorghum, rye, barley, brassica, sunflower, seaweeds, lemna, oat, soybean, cotton, legumes, rape/canola, alfalfa, flax, sunflower, safflower, brassica, cotton, flax, peanut, and clover; lettuce, tomato, cucurbits, cassava, potato, carrot, radish, pea, lentil, cabbage, cauliflower, broccoli, Brussel sprouts, peppers, other vegetables, citrus, apples, pears, peaches, apricots, walnuts, other fruit trees, orchids, carnations, roses, other flowers, cacao; poplar, elms, other deciduous trees, pine, Doaglas-fir, spruce, other conifers, turf grasses, cacao, rubber trees and members of the genus Hevea.

10. The plant cell of claim 9, wherein the plant cell is obtained from a Douglas-fir plant.

11. The plant cell of claim 9, wherein the plant cell is obtained from a wheat plant.

12. The plant cell of claim 9, wherein the plant cell is obtained from a potato plant.

13. The plant cell of claim 9, wherein the plant cell is obtained from a tobacco plant.

14. A method for expressing at least one protein in a host cell, comprising:

operably linking an ORF to the promoter of claim 1 to produce a transgene;

introducing the transgene into a vector; and introducing the vector into a host cell, wherein the host cell produces a protein from the ORF.

15. The method according to claim 14, wherein the host cell is a plant host cell.

16. The promoter of claim 1, wherein the promoter is inducible.

17. The promoter of claim 1, wherein the promoter is inducible at less than 20° C.

18. The promoter of claim 1, wherein the promoter is developmentally specific.

19. The promoter of claim 18, wherein the promoter is expressed in actively dividing cells.

20. The promoter of claim 1, wherein the promoter is wound-inducible.

21. The promoter of claim 1, wherein the promoter comprises a nucleic acid sequence sharing at least 95% sequence identity to SEQ ID NO: 18.

22. The promoter of claim 1, wherein the promoter comprises the nucleic acid sequence shown in SEQ ID NO: 18.

23. The promoter of claim 1, wherein the promoter comprises a nucleic acid sequence sharing at least 90% sequence identity to SEQ ID NO: 17.

24. The promoter of claim 1, wherein the promoter comprises a nucleic acid sequence sharing at least 95% sequence identity to SEQ ID NO: 17.

25. The promoter of claim 1, wherein the promoter comprises the nucleic acid sequence shown in SEQ ID NO: 17.

26. The promoter of claim 1, wherein the promoter comprises a nucleic acid sequence sharing at least 90% sequence identity to SEQ ID NO: 16.

27. The promoter of claim 1, wherein the promoter comprises a nucleic acid sequence sharing at least 95% sequence identity to SEQ ID NO: 16.

28. The promoter of claim 1, wherein the promoter comprises the nucleic acid sequence shown in SEQ ID NO: 16.

29. The promoter of claim 1, wherein the promoter comprises a nucleic acid sequence sharing at least 90% sequence identity to SEQ ID NO: 31.

30. The promoter of claim 1, wherein the promoter comprises a nucleic acid sequence sharing at least 95% sequence identity to SEQ ID NO: 31.

31. The promoter of claim 1, wherein the promoter comprises the nucleic acid sequence shoan in SEQ ID NO: 31.

* * * * *

UNITED STATES PATENT AND TRADEMARK OFFICE
CERTIFICATE OF CORRECTION

PATENT NO. : 6,440,674 B1
DATED : August 27, 2002
INVENTOR(S) : Santosh Misra and Benjamin S. Forward It is certified that error appears in the above-identified patent and that said Letters Patent is hereby corrected as shown below:

<u>Title page,</u>
Item [56], References Cited, OTHER PUBLICATIONS, in the second-listed document, "Tranberger" should be -- Tranbarger --.

<u>Column 3,</u>
Line 62, "15 ∞g" should be -- 15 $\mu$g --.

<u>Column 14,</u>
Line 32, "microsomal fraction)" should be -- (microsomal fraction) --.

<u>Column 15,</u>
Line 54, "mounts" should be -- amounts --.

<u>Column 19,</u>
Line 11, "20" should be deleted.

<u>Column 50,</u>
Line 28, "shoan" should be -- shown --.

Signed and Sealed this

Ninth Day of September, 2003

JAMES E. ROGAN
*Director of the United States Patent and Trademark Office*

SEQUENCE LISTING

```
<160> NUMBER OF SEQ ID NOS: 37

<210> SEQ ID NO 1
<211> LENGTH: 6
<212> TYPE: DNA
<213> ORGANISM: Artificial Sequence
<220> FEATURE:
<221> NAME/KEY: variation
<222> LOCATION: (3)..(4)
<223> OTHER INFORMATION: N = A, C, G, or T
<223> OTHER INFORMATION: Description of Artificial Sequence: PROMOTER
      ELEMENT

<400> SEQUENCE: 1 canntg                                                                 6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 2 gcatgc                                                                 6

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 3
aaaaattaat atttaatgtt aatattaat                                        29

<210> SEQ ID NO 4
<211> LENGTH: 4
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 4 acgt                                                                   4
```

```
<210> SEQ ID NO 5
<211> LENGTH: 9
<212> TYPE: DNA
<213> ORGANISM: Artificial Sequence
<220> FEATURE:
<221> NAME/KEY: variation
<222> LOCATION: (3)..(4)
<223> OTHER INFORMATION: N = A, C, G, and T
<223> OTHER INFORMATION: Description of Artificial Sequence: PROMOTER
      ELEMENT

<400> SEQUENCE: 5 ttnntcatc                                                                    9

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 6
aagattcctc taa                                                              13

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 7
gttgttgaga                                                                  10

<210> SEQ ID NO 8
<211> LENGTH: 4
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 8 tata                                                                         4

<210> SEQ ID NO 9
<211> LENGTH: 4
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 9 caat                                                                         4

<210> SEQ ID NO 10
<211> LENGTH: 6
<212> TYPE: DNA
<213> ORGANISM: Artificial Sequence
<220> FEATURE:
<221> NAME/KEY: variation
<222> LOCATION: (3)
<223> OTHER INFORMATION: W = a, t, or u
<223> OTHER INFORMATION: Description of Artificial Sequence: PROMOTER
      ELEMENT
```

```
<400> SEQUENCE: 10 ccwacc                                                                    6

<210> SEQ ID NO 11
<211> LENGTH: 6
<212> TYPE: DNA
<213> ORGANISM: Artificial Sequence
<220> FEATURE:
<221> NAME/KEY: variation
<222> LOCATION: (2)
<223> OTHER INFORMATION: R = g or a
<221> NAME/KEY: variation
<222> LOCATION: (3)..(6)
<223> OTHER INFORMATION: W = a, t, or u
<223> OTHER INFORMATION: Description of Artificial Sequence: PROMOTER
      ELEMENT

<400> SEQUENCE: 11 grwaaw                                                                    6

<210> SEQ ID NO 12
<211> LENGTH: 7
<212> TYPE: DNA
<213> ORGANISM: Artificial Sequence
<220> FEATURE:
<221> NAME/KEY: variation
<222> LOCATION: (2)
<223> OTHER INFORMATION: n=a, t, c, g, or u
<223> OTHER INFORMATION: Description of Artificial Sequence: PROMOTER
      ELEMENT

<400> SEQUENCE: 12 cnaacac                                                                   7

<210> SEQ ID NO 13
<211> LENGTH: 11
<212> TYPE: DNA
<213> ORGANISM: Artificial Sequence
<220> FEATURE:
<221> NAME/KEY: variation
<222> LOCATION: (1)..(11)
<223> OTHER INFORMATION: w = a, t, or u
<221> NAME/KEY: variation
<222> LOCATION: (7)
<223> OTHER INFORMATION: r = a or g
<223> OTHER INFORMATION: Description of Artificial Sequence: PROMOTER
      ELEMENT

<400> SEQUENCE: 13
wtttatrttt w                                                             11

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 14 ttcgtcatc                                                                 9

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence: PROMOTER
```

ELEMENT

<400> SEQUENCE: 15 tttatcatc                                                                                   9

<210> SEQ ID NO 16
<211> LENGTH: 2263
<212> TYPE: DNA
<213> ORGANISM: Pseudotsuga menziesii

<400> SEQUENCE: 16

| tcaactaagt | ccttaatgtc | ccgagctttt | ttcttcaccg | accaagatat | aaacacatct |   60 |
| tttaaactct | taaggttcac | aacaaactga | gatgcaggag | atacctctga | actggcatca |  120 |
| taaactttcc | aggatgcttt | taataatgct | accaggtcat | catcagctaa | ccaacaagca |  180 |
| ttaaacttga | agggactaca | agacctgata | tcattattca | gaatttgtaa | ataaacaagc |  240 |
| tgactcgatt | agaataccct | ccacacccaa | cccactgtct | aaaataaaga | tcacaatcca |  300 |
| agagatcggc | cgaaataagt | aaccgatcca | atcttttact | tatgttctta | gacctaactc |  360 |
| tttgattaga | ccatgttggg | agagtaacaa | catgaacaat | atccactaga | ccaaatcctt |  420 |
| ccaactgttt | aatgaagaaa | tcagttaata | catctactct | agctttgact | ccccaaactt |  480 |
| cggagtatct | cagggagaaa | ttcagatccc | caccaaaaat | caatttaggg | cacctaaaac |  540 |
| attccaattt | cagcagatta | ttccagaata | attccctatc | caaacaagga | ccgtacagat |  600 |
| tcacaaaaca | taaatccatc | tgtagctcaa | tagaataaag | tacaatacac | aagtcagaac |  660 |
| acaaagccca | tgcattgagc | aaatgaaatt | taagagtcct | ccaccccaaa | aataaacccc |  720 |
| cagatctacc | cttggcatcc | actgacacaa | actttcaatt | ctttaacatt | gtctccaact |  780 |
| ctcccaccaa | aataacccca | tcacacatcg | tttcttgcaa | gaaaattaca | tctaaaaatt |  840 |
| gctcatcaat | caacctacgc | acaactagtt | ttttaggtat | actagccaaa | ccctatagt  |  900 |
| tgagggtcat | caatcataat | ggaacctctg | agggggcaaa | cactgcgcta | agtgcccag  |  960 |
| taacagtctt | cacttaagaa | agcatagttg | gcataagata | atcactaccc | tgaacaaaag | 1020 |
| gatgggtcca | taaagctctc | gttctgtacc | acacacacgt | tcttcgttaa | ccttaaaaca | 1080 |
| agaccgaagg | aaataacccct | cactgactac | aggattgcct | ttgtgcagag | atacaaaccc | 1140 |
| tagatccccc | aatgcaaaat | cagacagagc | caaattgcaa | gatgaaagat | tacccacaac | 1200 |
| aaaaccctcg | atgttcttat | ccaacaccgg | ttctccaaac | tcagataacg | aggaaataca | 1260 |
| taagggttta | agagacttca | tatagataga | ctgagaccct | aaattcacct | catcaattaa | 1320 |
| tggattagga | gaaaggttcg | tatccaccaa | cccatcaatc | ttgacaataa | ccggcttatc | 1380 |
| cccagatgta | tgccctccat | tcttaacacg | ccaaacagat | ttggtcttat | agacagaacc | 1440 |
| agagttaggt | tttttcctaa | aaggtagaga | acaatcatgg | atcaaatggc | cataaacatg | 1500 |
| gcatctatta | cgccgaaatg | ggatgcccaa | ataatccaag | ggttgactaa | actcataatt | 1560 |
| acccctttta | atcattaatt | caggaacaag | gaagaaagaa | gttacatatc | tccaatttat | 1620 |
| ctaatttatg | ttttttttat | atacatgctc | ttgtaaatgt | tttaaatctc | taaatggtat | 1680 |
| aatacgcatc | ttctacgcaa | atatcattcg | atttattttc | ctatatgttt | tcttacatgg | 1740 |
| catcaagtcc | acgtgtagta | ttgccattta | gttaatagat | cacacacgtg | tccaagtgca | 1800 |
| attggttcga | acacctcaag | ttttcaataa | taatggacga | gcaggaaatg | tgggtaattc | 1860 |
| ggagtggttg | gtcgagacct | tccccagtat | cttatcacca | tgaactaata | tttcgaggcg | 1920 |
| gtgacctaaa | acaagaaaa  | taaattaaaa | gacccattca | attttaccca | ccgctttttcc | 1980 |

| | |
|---|---|
| tacgaggcac taggactaca gggaactctc gtaacacgtg tcaataagcg attggctcaa | 2040 |
| acacgtcaat tttttaaaat agctctcaac tccgaacggg taacgtggcg aaatatgagt | 2100 |
| ggaagtactc gacacgtgtt ggaaagcgat gcgttcagtg acgcatagtg aatttacggg | 2160 |
| aaagtagatg attctggaag aggtttctag gagcagagta ataagattgt agaagggcac | 2220 |
| cataaatcca ttgctctgtg acaaatcctt caaatttgga cgc | 2263 |

<210> SEQ ID NO 17
<211> LENGTH: 1259
<212> TYPE: DNA
<213> ORGANISM: Pseudotsuga menziesii

<400> SEQUENCE: 17

| | |
|---|---|
| taccctgaac aaaaggatgg gtccataaag ctctcgttct gtaccacaca cacgttcttc | 60 |
| gttaacctta aaacaagacc gaaggaaata accctcactg actacaggat tgcctttgtg | 120 |
| cagagataca aaccctagat cccccaatgc aaaatcagac agagccaaat tgcaagatga | 180 |
| aagattaccc acaacaaaac cctcgatgtt cttatccaac accggttctc caaactcaga | 240 |
| taacgaggaa atacataagg gtttaagaga cttcatatag atagactgag accctaaatt | 300 |
| cacctcatca attaatggat taggagaaag gttcgtatcc accaacccat caatcttgac | 360 |
| aataaccggc ttatccccag atgtatgccc tccattctta acacgccaaa cagatttggt | 420 |
| cttatagaca gaaccagagt taggtttttt cctaaaaggt agagaacaat catggatcaa | 480 |
| atggccataa acatggcatc tattacgccg aaatgggatg cccaaataat ccaagggttg | 540 |
| actaaactca taattacccc ttttaatcat taattcagga acaaggaaga agaagttac | 600 |
| atatctccaa tttatctaat ttatgttttt tttatataca tgctcttgta aatgtttaa | 660 |
| atctctaaat ggtataatac gcatcttcta cgcaaatatc attcgattta ttttcctata | 720 |
| tgttttctta catggcatca agtccacgtg tagtattgcc atttagttaa tagatcacac | 780 |
| acgtgtccaa gtgcaattgg ttcgaacacc tcaagttttc aataataatg gacgagcagg | 840 |
| aaatgtgggt aattcggagt ggttggtcga gaccttcccc agtatcttat caccatgaac | 900 |
| taatatttcg aggcggtgac ctaaaacaaa gaaaataaat taaaagaccc attcaattt | 960 |
| acccaccgct tttcctacga ggcactagga ctacagggaa ctctcgtaac acgtgtcaat | 1020 |
| aagcgattgg ctcaaacacg tcaatttttt aaaatagctc tcaactccga acgggtaacg | 1080 |
| tggcgaaata tgagtggaag tactcgacac gtgttggaaa gcgatgcgtt cagtgacgca | 1140 |
| tagtgaattt acgggaaagt agatgattct ggaagaggtt tctaggagca gagtaataag | 1200 |
| attgtagaag ggcaccataa atccattgct ctgtgacaaa tccttcaaat ttggacgcg | 1259 |

<210> SEQ ID NO 18
<211> LENGTH: 263
<212> TYPE: DNA
<213> ORGANISM: Pseudotsuga menziesii

<400> SEQUENCE: 18

| | |
|---|---|
| ggaactctcg taacacgtgt caataagcga ttggctcaaa cacgtcaatt ttttaaaata | 60 |
| gctctcaact ccgaacgggt aacgtggcga aatatgagtg gaagtactcg acacgtgttg | 120 |
| gaaagcgatg cgttcagtga cgcatagtga atttacggga agtagatga ttctggaaga | 180 |
| ggtttctagg agcagagtaa taagattgta gaagggcacc ataaatccat tgctctgtga | 240 |
| caaatccttc aaatttggac gcg | 263 |

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: PCR PRIMERS

<400> SEQUENCE: 19
aatgaaagcg aagtgacacc                                            20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: PCR PRIMERS

<400> SEQUENCE: 20
cagaaccatt aacaagagca agat                                       24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: PCR PRIMERS

<400> SEQUENCE: 21
aaccagcagt gataaacgcc                                            20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: PCR PRIMERS

<400> SEQUENCE: 22
tatggtttgg ataaaaaggg ag                                         22

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: PCR PRIMER

<400> SEQUENCE: 23
tcgaagcgca aatctagagt ttaaacttcc                                 30

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: PCR PRIMERS

<400> SEQUENCE: 24
aagaaggcaa gctttcaact aa                                         22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: PCR PRIMERS

```
<400> SEQUENCE: 25
gcataagaaa gcttctaccc tg                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 26
gcactaggaa gcttgggaac tc                                              22

<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 27 acgtca                                                                 6

<210> SEQ ID NO 28
<211> LENGTH: 8
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 28 gtgccctt                                                               8

<210> SEQ ID NO 29
<211> LENGTH: 5
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 29 agaaa                                                                  5

<210> SEQ ID NO 30
<211> LENGTH: 5
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 30 atatt                                                                  5

<210> SEQ ID NO 31
<211> LENGTH: 2277
<212> TYPE: DNA
<213> ORGANISM: Pseudotsuga menziesii

<400> SEQUENCE: 31
tctagatcaa ctaagtcctt aatgtcccga gcttttttct tcaccgacca agatataaac     60
```

-continued

```
acatctttta aactcttaag gttcacaaca aactgagatg caggagatac ctctgaactg    120
gcatcataaa ctttccagga tgcttttaat aatgctacca ggtcatcatc agctaaccaa    180
caagcattaa acttgaaggg actacaagac ctgatatcat tattcagaat ttgtaaataa    240
acaagctgac tcgattagaa taccctccac acccaaccca ctgtctaaaa taaagatcac    300
aatccaagag atcggccgaa ataagtaacc gatccaatct tttacttatg ttcttagacc    360
taactctttg attagaccat gttgggagag taacaacatg aacaatatcc actagaccaa    420
atccttccaa ctgtttaatg aagaaatcag ttaatacatc tactctagct ttgactcccc    480
aaacttcgga gtatctcagg gagaaattca gatccccacc aaaaatcaat ttagggcacc    540
taaaacattc caatttcagc agattattcc agaataattc cctatccaaa caaggaccgt    600
acagattcac aaaacataaa tccatctgta gctcaataga ataaagtaca atacacaagt    660
cagaacacaa agcccatgca ttgagcaaat gaaatttaag agtcctccac cccaaaaata    720 aaccccccaga tctaccccttg gcatccactg acacaaactt tcaattcttt aacattgtct   780
ccaactctcc caccaaaata accccatcac acatcgtttc ttgcaagaaa attacatcta    840
aaaattgctc atcaatcaac ctacgcacaa ctagtttttt aggtatacta gccaaacccc    900
tatagttgag ggtcatcaat cataatggaa cctctgaggg ggcaaacact gcgctaagtg    960
ccccagtaac agtcttcact taagaaagca tagttggcat aagataatca ctaccctgaa   1020 caaaggatg ggtccataaa gctctcgttc tgtaccacac acacgttctt cgttaaccctt   1080 aaaacaagac cgaaggaaat aaccctcact gactacagga ttgcctttgt gcagagatac   1140
aaaccctaga tcccccaatg caaaatcaga cagagccaaa ttgcaagatg aaagattacc   1200
cacaacaaaa ccctcgatgt tcttatccaa caccggttct ccaaactcag ataacgagga   1260
aatacataag ggtttaagag acttcatata gatagactga gaccctaaat tcacctcatc   1320
aattaatgga ttaggagaaa ggttcgtatc caccaaccca tcaatcttga caataaccgg   1380
cttatcccca gatgtatgcc ctccattctt aacacgccaa acagatttgg tcttatagac   1440
agaaccagag ttaggttttt tcctaaaagg tagagaacaa tcatggatca aatggccata   1500
aacatggcat ctattacgcc gaaatgggat gcccaaataa tccaagggtt gactaaactc   1560
ataattaccc cttttaatca ttaattcagg aacaaggaag aaagaagtta catatctcca   1620
atttatctaa tttatgtttt tttatatac atgctcttgt aaatgtttta aatctctaaa    1680
tggtataata cgcatcttct acgcaaatat cattcgattt attttcctat atgttttctt    1740
acatggcatc aagtccacgt gtagtattgc catttagtta atagatcaca cacgtgtcca    1800
agtgcaattg gttcgaacac ctcaagtttt caataataat ggacgagcag gaaatgtggg    1860
taattcggag tggttggtcg agaccttccc cagtatctta tcaccatgaa ctaatatttc    1920
gaggcggtga cctaaaacaa agaaaataaa ttaaaagacc cattcaattt tacccaccgc    1980
ttttcctacg aggcactagg actacaggga actctcgtaa cacgtgtcaa taagcgattg    2040
gctcaaacac gtcaattttt taaaatagct ctcaactccg aacgggtaac gtggcgaaat    2100
atgagtggaa gtactcgaca cgtgttggaa agcgatgcgt tcagtgacgc atagtgaatt    2160
tacgggaaag tagatgattc tggaagaggt ttctaggagc agagtaataa gattgtagaa    2220
gggcaccata aatccattgc tctgtgacaa atccttcaaa tttggacgcg aaacgcg       2277
```

<210> SEQ ID NO 32
<211> LENGTH: 7
<212> TYPE: DNA
<213> ORGANISM: Artificial Sequence -continued

```
<220> FEATURE:
<223> OTHER INFORMATION: Description of Artificial Sequence: PROMOTER
      ELEMENTS

<400> SEQUENCE: 32 caaacac                                                                   7

<210> SEQ ID NO 33
<211> LENGTH: 7
<212> TYPE: DNA
<213> ORGANISM: Artificial Sequence
<220> FEATURE:
<223> OTHER INFORMATION: Description of Artificial Sequence: PROMOTER
      ELEMENTS

<400> SEQUENCE: 33 acgtggc                                                                   7

<210> SEQ ID NO 34
<211> LENGTH: 5
<212> TYPE: DNA
<213> ORGANISM: Artificial Sequence
<220> FEATURE:
<223> OTHER INFORMATION: Description of Artificial Sequence: PROMOTER
      ELEMENTS

<400> SEQUENCE: 34 tgacg                                                                     5

<210> SEQ ID NO 35
<211> LENGTH: 2626
<212> TYPE: DNA
<213> ORGANISM: Pseudotsuga menziesii
<220> FEATURE:
<221> NAME/KEY: CDS
<222> LOCATION: (374)..(2338)

<400> SEQUENCE: 35
gaagctgccg tggtcgcaga taatgcaatt gcaatgctga ggtttctctg agaggatcga         60
tagtcgggac gattttctct gtttcgatac atatcctttc gcttttcaac gatatcgctt        120
cgttttcagc catttaattc gcatacgtga acgaagatcg ccgcagtga aggttatctt         180 gtcgatttcg ctgttgtgag cttttgcac tgcgataaca caccaatagg tgtcacttcg         240
ctttcattca cgaggtattg aggttgcttc tgcttaaaat ttgatgcgcg agggttttgg        300
aaaggcgcca gccatgggac ggaagcagaa atgcgctggg ttcaacaacg ctggaaaaga       360
tttcaacggc ttt atg ttc ctt gcg gcg ttt atc act gct ggt ttt ctt          409
            Met Phe Leu Ala Ala Phe Ile Thr Ala Gly Phe Leu
             1               5                  10 ttc agc tct gtt att gct gca gaa gaa gca gca aag tta gga aca gta         457
Phe Ser Ser Val Ile Ala Ala Glu Glu Ala Ala Lys Leu Gly Thr Val
         15                  20                  25 att ggt ata gat ctc gga acc acg tat tct tgt gtt ggt gtt tac aaa         505
Ile Gly Ile Asp Leu Gly Thr Thr Tyr Ser Cys Val Gly Val Tyr Lys
     30                  35                  40 aat ggt cat gtt gaa atc ata gca aat gac caa gga aat agg att aca         553
Asn Gly His Val Glu Ile Ile Ala Asn Asp Gln Gly Asn Arg Ile Thr
 45                  50                  55                  60 cct tct tgg gtt gcc ttc act gat acc gaa aga ctc atc gga gag gct         601
Pro Ser Trp Val Ala Phe Thr Asp Thr Glu Arg Leu Ile Gly Glu Ala
                 65                  70                  75 gcc aaa aac cag gcg gca atg aat cct gaa agg acc gtt ttt gat gtg         649
Ala Lys Asn Gln Ala Ala Met Asn Pro Glu Arg Thr Val Phe Asp Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 80  |     |     |     |     | 85  |     |     |     |     | 90  |     |      |
| aaa | cgg | ttg | att | gga | aga | aag | tat | gag | gac | aag | gag | gtg | caa | aaa | gac | 697  |
| Lys | Arg | Leu | Ile | Gly | Arg | Lys | Tyr | Glu | Asp | Lys | Glu | Val | Gln | Lys | Asp |      |
|     |     |     |     | 95  |     |     |     |     | 100 |     |     |     |     | 105 |     |      |
| atc | aaa | ctt | ttg | ccc | tac | aaa | att | gta | aac | aaa | gat | ggg | aag | cct | tac | 745  |
| Ile | Lys | Leu | Leu | Pro | Tyr | Lys | Ile | Val | Asn | Lys | Asp | Gly | Lys | Pro | Tyr |      |
|     | 110 |     |     |     |     | 115 |     |     |     |     | 120 |     |     |     |     |      |
| att | cag | gtg | aag | atc | agg | gat | ggt | gaa | atc | aaa | gtt | ttt | agt | ccc | gag | 793  |
| Ile | Gln | Val | Lys | Ile | Arg | Asp | Gly | Glu | Ile | Lys | Val | Phe | Ser | Pro | Glu |      |
| 125 |     |     |     |     | 130 |     |     |     |     | 135 |     |     |     |     | 140 |      |
| gaa | att | agt | gca | atg | att | ttg | ttg | aaa | atg | aag | gaa | aca | gct | gag | tcc | 841  |
| Glu | Ile | Ser | Ala | Met | Ile | Leu | Leu | Lys | Met | Lys | Glu | Thr | Ala | Glu | Ser |      |
|     |     |     |     | 145 |     |     |     |     | 150 |     |     |     |     | 155 |     |      |
| tac | ctt | gga | agg | aaa | atc | aag | gat | gca | gtt | gtt | aca | gtt | cca | gca | tat | 889  |
| Tyr | Leu | Gly | Arg | Lys | Ile | Lys | Asp | Ala | Val | Val | Thr | Val | Pro | Ala | Tyr |      |
|     |     |     |     | 160 |     |     |     |     | 165 |     |     |     |     | 170 |     |      |
| ttc | aat | gat | gca | caa | aga | cag | gcc | acc | aag | gat | gct | ggt | gta | att | gct | 937  |
| Phe | Asn | Asp | Ala | Gln | Arg | Gln | Ala | Thr | Lys | Asp | Ala | Gly | Val | Ile | Ala |      |
|     |     |     | 175 |     |     |     |     | 180 |     |     |     |     | 185 |     |     |      |
| ggg | tta | aat | gtt | gct | cgt | ata | ata | aat | gag | cca | act | gct | gca | gca | att | 985  |
| Gly | Leu | Asn | Val | Ala | Arg | Ile | Ile | Asn | Glu | Pro | Thr | Ala | Ala | Ala | Ile |      |
|     | 190 |     |     |     |     | 195 |     |     |     |     | 200 |     |     |     |     |      |
| gca | tat | ggt | ttg | gat | aaa | aag | gga | gga | gaa | aag | aac | att | ctt | gtt | tat | 1033 |
| Ala | Tyr | Gly | Leu | Asp | Lys | Lys | Gly | Gly | Glu | Lys | Asn | Ile | Leu | Val | Tyr |      |
| 205 |     |     |     |     | 210 |     |     |     |     | 215 |     |     |     |     | 220 |      |
| gac | ctt | gga | ggt | gga | act | ttt | gat | gtc | agt | att | ctc | acc | att | gat | aat | 1081 |
| Asp | Leu | Gly | Gly | Gly | Thr | Phe | Asp | Val | Ser | Ile | Leu | Thr | Ile | Asp | Asn |      |
|     |     |     |     | 225 |     |     |     |     | 230 |     |     |     |     | 235 |     |      |
| ggt | gtt | ttt | gaa | gtg | ttg | tca | acc | agc | ggg | gat | act | cat | tta | gga | gga | 1129 |
| Gly | Val | Phe | Glu | Val | Leu | Ser | Thr | Ser | Gly | Asp | Thr | His | Leu | Gly | Gly |      |
|     |     |     | 240 |     |     |     |     | 245 |     |     |     |     | 250 |     |     |      |
| gag | gac | ttc | gat | caa | cga | gtt | atg | gat | tac | ttc | att | aaa | ttg | gtc | aag | 1177 |
| Glu | Asp | Phe | Asp | Gln | Arg | Val | Met | Asp | Tyr | Phe | Ile | Lys | Leu | Val | Lys |      |
|     |     | 255 |     |     |     |     | 260 |     |     |     |     | 265 |     |     |     |      |
| aaa | aaa | cac | aac | aaa | gat | att | agc | aag | gat | aac | aga | gct | ctt | ggc | aaa | 1225 |
| Lys | Lys | His | Asn | Lys | Asp | Ile | Ser | Lys | Asp | Asn | Arg | Ala | Leu | Gly | Lys |      |
|     | 270 |     |     |     |     | 275 |     |     |     |     | 280 |     |     |     |     |      |
| ctt | agg | agg | gag | tgt | gag | agg | gcc | aaa | aga | gct | ctg | agc | agc | cag | cat | 1273 |
| Leu | Arg | Arg | Glu | Cys | Glu | Arg | Ala | Lys | Arg | Ala | Leu | Ser | Ser | Gln | His |      |
| 285 |     |     |     |     | 290 |     |     |     |     | 295 |     |     |     |     | 300 |      |
| caa | gtt | cgt | gtt | gaa | att | gaa | tca | ctt | ttt | gat | ggt | gtt | gat | ttt | tca | 1321 |
| Gln | Val | Arg | Val | Glu | Ile | Glu | Ser | Leu | Phe | Asp | Gly | Val | Asp | Phe | Ser |      |
|     |     |     |     | 305 |     |     |     |     | 310 |     |     |     |     | 315 |     |      |
| gaa | cca | tta | aca | aga | gca | aga | ttc | gag | gaa | ctc | aat | atg | gac | ctc | ttc | 1369 |
| Glu | Pro | Leu | Thr | Arg | Ala | Arg | Phe | Glu | Glu | Leu | Asn | Met | Asp | Leu | Phe |      |
|     |     |     | 320 |     |     |     |     | 325 |     |     |     |     | 330 |     |     |      |
| aag | aaa | act | ctt | ggg | cca | gta | aag | aag | gct | cta | gat | gat | gct | aac | ttg | 1417 |
| Lys | Lys | Thr | Leu | Gly | Pro | Val | Lys | Lys | Ala | Leu | Asp | Asp | Ala | Asn | Leu |      |
|     |     | 335 |     |     |     |     | 340 |     |     |     |     | 345 |     |     |     |      |
| cag | aag | act | gaa | att | aat | gaa | ctt | gtg | ctt | gtt | gga | gga | agt | act | cgc | 1465 |
| Gln | Lys | Thr | Glu | Ile | Asn | Glu | Leu | Val | Leu | Val | Gly | Gly | Ser | Thr | Arg |      |
|     | 350 |     |     |     |     | 355 |     |     |     |     | 360 |     |     |     |     |      |
| ata | cca | aag | gtt | cag | caa | tta | ttg | aag | gac | tta | ttt | gat | ggc | aag | gag | 1513 |
| Ile | Pro | Lys | Val | Gln | Gln | Leu | Leu | Lys | Asp | Leu | Phe | Asp | Gly | Lys | Glu |      |
| 365 |     |     |     |     | 370 |     |     |     |     | 375 |     |     |     |     | 380 |      |
| cct | aac | aaa | ggt | gtt | aat | cca | gat | gaa | gct | gtg | gct | tat | ggg | gct | gct | 1561 |
| Pro | Asn | Lys | Gly | Val | Asn | Pro | Asp | Glu | Ala | Val | Ala | Tyr | Gly | Ala | Ala |      |
|     |     |     |     | 385 |     |     |     |     | 390 |     |     |     |     | 395 |     |      |
| gtt | cag | ggt | ggt | att | ctg | agt | ggt | gag | gga | ggt | gac | gaa | aca | aaa | gat | 1609 |

```
Val Gln Gly Gly Ile Leu Ser Gly Glu Gly Gly Asp Glu Thr Lys Asp
            400                 405                 410 att ctt cta ttg gat gtt gct ccc ctc agc cta ggt ata gaa act gtt       1657
Ile Leu Leu Leu Asp Val Ala Pro Leu Ser Leu Gly Ile Glu Thr Val
        415                 420                 425 ggt gga gta atg acc aaa ctt att ccg agg aac act gtc att cca aca       1705
Gly Gly Val Met Thr Lys Leu Ile Pro Arg Asn Thr Val Ile Pro Thr
    430                 435                 440 aag aag tca caa gtg ttc aca act tat caa gat cag caa acc act gtt       1753
Lys Lys Ser Gln Val Phe Thr Thr Tyr Gln Asp Gln Gln Thr Thr Val
445                 450                 455                 460 tca atc aag gtt tat gaa gga gag cgg agt ctt aca aag gat tgc cga       1801
Ser Ile Lys Val Tyr Glu Gly Glu Arg Ser Leu Thr Lys Asp Cys Arg
                465                 470                 475 gaa tta ggc aaa ttt gat ctg tct gga atc cct cca gct cct cgt ggt       1849
Glu Leu Gly Lys Phe Asp Leu Ser Gly Ile Pro Pro Ala Pro Arg Gly
            480                 485                 490 gtg cca cag att gag gtc acc ttt gag gtt gat gcc aac ggt atc ctc       1897
Val Pro Gln Ile Glu Val Thr Phe Glu Val Asp Ala Asn Gly Ile Leu
        495                 500                 505 aat gta aga gca gag gac aag ggc acc aag aaa acc gaa aag att acc       1945
Asn Val Arg Ala Glu Asp Lys Gly Thr Lys Lys Thr Glu Lys Ile Thr
    510                 515                 520 atc aca aat gac aaa ggt aga ttg agc cag gaa gaa ata gaa aga atg       1993
Ile Thr Asn Asp Lys Gly Arg Leu Ser Gln Glu Glu Ile Glu Arg Met
525                 530                 535                 540 gtc aag gag gca gag gag ttt gca gag gag gat aag aaa gtg aag gac       2041
Val Lys Glu Ala Glu Glu Phe Ala Glu Glu Asp Lys Lys Val Lys Asp
                545                 550                 555 aaa att gat gcg agg aac aat ctt gaa aca tat gtc tac aac atg aaa       2089
Lys Ile Asp Ala Arg Asn Asn Leu Glu Thr Tyr Val Tyr Asn Met Lys
            560                 565                 570 agc acc att aat gag aag gat aaa ttg gca gat aaa att gat tcc gaa       2137
Ser Thr Ile Asn Glu Lys Asp Lys Leu Ala Asp Lys Ile Asp Ser Glu
        575                 580                 585 gac aag gag aag atc gaa act gct atc aaa gaa gca ttg gaa tgg ctt       2185
Asp Lys Glu Lys Ile Glu Thr Ala Ile Lys Glu Ala Leu Glu Trp Leu
    590                 595                 600 gat gac aac cag tcg gct gag aag gag gac ttc gag gag aag ttg aaa       2233
Asp Asp Asn Gln Ser Ala Glu Lys Glu Asp Phe Glu Glu Lys Leu Lys
605                 610                 615                 620 gag gtg gaa gct gta tgc agt ccc atc atc aag caa gta tat gag aaa       2281
Glu Val Glu Ala Val Cys Ser Pro Ile Ile Lys Gln Val Tyr Glu Lys
                625                 630                 635 act gga gga gga tct tct gga ggc gat gat gaa gac gag gac tcg cat       2329
Thr Gly Gly Gly Ser Ser Gly Gly Asp Asp Glu Asp Glu Asp Ser His
            640                 645                 650 gaa gaa ctc taagccattt cagtttctgt tgaattttag ttgtacaaat              2378
Glu Glu Leu
        655 cacgatgaac taattctaca gaagagatct ctgagcataa tagggtttat gaggatgatt     2438 ggcaacgaac aagagattca actgatgaaa gtcaaatgac tgtttgtttt ttctatcaat     2498 cagaatgtta tttcacaga ttgaaattgg caacgaacaa gagattcaac tgatgaaagt      2558 caaatgacta tttgtttgtt ttttctatca atcagaatgt tattttcaca gattttttcaa    2618 tctgtagt                                                              2626
```

<210> SEQ ID NO 36

```
<211> LENGTH: 655
<212> TYPE: PRT
<213> ORGANISM: Pseudotsuga menziesii

<400> SEQUENCE: 36
```

| | | | | | | | | | | | | | | |
|---|---|---|---|---|---|---|---|---|---|---|---|---|---|---|
| Met | Phe | Leu | Ala | Ala | Phe | Ile | Thr | Ala | Gly | Phe | Leu | Phe | Ser | Ser | Val |
| 1 | | | | 5 | | | | | 10 | | | | | 15 | |

Ile Ala Ala Glu Glu Ala Ala Lys Leu Gly Thr Val Ile Gly Ile Asp
              20                  25                  30

Leu Gly Thr Thr Tyr Ser Cys Val Gly Val Tyr Lys Asn Gly His Val
          35                  40                  45

Glu Ile Ile Ala Asn Asp Gln Gly Asn Arg Ile Thr Pro Ser Trp Val
      50                  55                  60

Ala Phe Thr Asp Thr Glu Arg Leu Ile Gly Glu Ala Ala Lys Asn Gln
 65                  70                  75                  80

Ala Ala Met Asn Pro Glu Arg Thr Val Phe Asp Val Lys Arg Leu Ile
              85                  90                  95

Gly Arg Lys Tyr Glu Asp Lys Glu Val Gln Lys Asp Ile Lys Leu Leu
            100                 105                 110

Pro Tyr Lys Ile Val Asn Lys Asp Gly Lys Pro Tyr Ile Gln Val Lys
        115                 120                 125

Ile Arg Asp Gly Glu Ile Lys Val Phe Ser Pro Glu Glu Ile Ser Ala
130                 135                 140

Met Ile Leu Leu Lys Met Lys Glu Thr Ala Glu Ser Tyr Leu Gly Arg
145                 150                 155                 160

Lys Ile Lys Asp Ala Val Val Thr Val Pro Ala Tyr Phe Asn Asp Ala
                165                 170                 175

Gln Arg Gln Ala Thr Lys Asp Ala Gly Val Ile Ala Gly Leu Asn Val
            180                 185                 190

Ala Arg Ile Ile Asn Glu Pro Thr Ala Ala Ala Ile Ala Tyr Gly Leu
        195                 200                 205

Asp Lys Lys Gly Gly Glu Lys Asn Ile Leu Val Tyr Asp Leu Gly Gly
    210                 215                 220

Gly Thr Phe Asp Val Ser Ile Leu Thr Ile Asp Asn Gly Val Phe Glu
225                 230                 235                 240

Val Leu Ser Thr Ser Gly Asp Thr His Leu Gly Gly Glu Asp Phe Asp
                245                 250                 255

Gln Arg Val Met Asp Tyr Phe Ile Lys Leu Val Lys Lys His Asn
            260                 265                 270

Lys Asp Ile Ser Lys Asp Asn Arg Ala Leu Gly Lys Leu Arg Arg Glu
        275                 280                 285

Cys Glu Arg Ala Lys Arg Ala Leu Ser Ser Gln His Gln Val Arg Val
290                 295                 300

Glu Ile Glu Ser Leu Phe Asp Gly Val Asp Phe Ser Glu Pro Leu Thr
305                 310                 315                 320

Arg Ala Arg Phe Glu Glu Leu Asn Met Asp Leu Phe Lys Lys Thr Leu
                325                 330                 335

Gly Pro Val Lys Lys Ala Leu Asp Asp Ala Asn Leu Gln Lys Thr Glu
            340                 345                 350

Ile Asn Glu Leu Val Leu Val Gly Gly Ser Thr Arg Ile Pro Lys Val
        355                 360                 365

Gln Gln Leu Leu Lys Asp Leu Phe Asp Gly Lys Glu Pro Asn Lys Gly
    370                 375                 380

Val Asn Pro Asp Glu Ala Val Ala Tyr Gly Ala Ala Val Gln Gly Gly

```
                            -continued
385                 390                 395                 400

Ile Leu Ser Gly Glu Gly Asp Glu Thr Lys Asp Ile Leu Leu Leu
                405                 410                 415

Asp Val Ala Pro Leu Ser Leu Gly Ile Glu Thr Val Gly Val Met
            420                 425                 430

Thr Lys Leu Ile Pro Arg Asn Thr Val Ile Pro Thr Lys Lys Ser Gln
        435                 440                 445

Val Phe Thr Thr Tyr Gln Asp Gln Gln Thr Thr Val Ser Ile Lys Val
    450                 455                 460

Tyr Glu Gly Glu Arg Ser Leu Thr Lys Asp Cys Arg Glu Leu Gly Lys
465                 470                 475                 480

Phe Asp Leu Ser Gly Ile Pro Pro Ala Pro Arg Gly Val Pro Gln Ile
                485                 490                 495

Glu Val Thr Phe Glu Val Asp Ala Asn Gly Ile Leu Asn Val Arg Ala
                500                 505                 510

Glu Asp Lys Gly Thr Lys Lys Thr Glu Lys Ile Thr Ile Thr Asn Asp
            515                 520                 525

Lys Gly Arg Leu Ser Gln Glu Glu Ile Glu Arg Met Val Lys Glu Ala
    530                 535                 540

Glu Glu Phe Ala Glu Glu Asp Lys Lys Val Lys Asp Lys Ile Asp Ala
545                 550                 555                 560

Arg Asn Asn Leu Glu Thr Tyr Val Tyr Asn Met Lys Ser Thr Ile Asn
                565                 570                 575

Glu Lys Asp Lys Leu Ala Asp Lys Ile Asp Ser Glu Asp Lys Glu Lys
            580                 585                 590

Ile Glu Thr Ala Ile Lys Glu Ala Leu Glu Trp Leu Asp Asp Asn Gln
    595                 600                 605

Ser Ala Glu Lys Glu Asp Phe Glu Glu Lys Leu Lys Glu Val Glu Ala
    610                 615                 620

Val Cys Ser Pro Ile Ile Lys Gln Val Tyr Glu Lys Thr Gly Gly Gly
625                 630                 635                 640

Ser Ser Gly Gly Asp Asp Glu Asp Glu Asp Ser His Glu Glu Leu
                645                 650                 655

<210> SEQ ID NO 37
<211> LENGTH: 4
<212> TYPE: PRT
<213> ORGANISM: Pseudotsuga menziesii

<400> SEQUENCE: 37

His Glu Glu Leu
  1
```